(12) United States Patent
Minor et al.

(10) Patent No.: US 7,191,106 B2
(45) Date of Patent: Mar. 13, 2007

(54) METHOD AND SYSTEM FOR PREDICTING MULTI-VARIABLE OUTCOMES

(75) Inventors: James M. Minor, Los Altos, CA (US); Mika Illouz, Palo Alto, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 729 days.

(21) Appl. No.: 10/400,372

(22) Filed: Mar. 27, 2003

(65) Prior Publication Data

US 2004/0083452 A1    Apr. 29, 2004

Related U.S. Application Data

(60) Provisional application No. 60/368,586, filed on Mar. 29, 2002.

(51) Int. Cl.
*G06F 7/60*    (2006.01)
*G06F 17/10*    (2006.01)

(52) U.S. Cl. .................... 703/2; 702/189; 702/196
(58) Field of Classification Search .......... 703/2; 702/189, 196
See application file for complete search history.

(56) References Cited

U.S. PATENT DOCUMENTS

| | | | | |
|---|---|---|---|---|
| 5,463,548 | A | * | 10/1995 | Asada et al. ............ 600/300 |
| 5,687,716 | A | * | 11/1997 | Kaufmann et al. ...... 600/300 |
| 5,860,917 | A | | 1/1999 | Comanor et al. |
| 6,260,005 | B1 | * | 7/2001 | Yang et al. .............. 703/11 |

OTHER PUBLICATIONS

Wold et al, "PLS-Regresson: A Basic Tool of Chemometrics", Chemometrics and Intelligent Laboratory Systems, vol. 58, Issue 2, Oct. 28, 2001, pp. 109-130.*
Gabrielsson et al, "Multivariate Methods in Pharmaceutical Applications", Journal of Chemometrics, vol. 16, 2002, pp. 141-160.*
Berkey et al, "Meta-Analysis of Multiple Outcomes by Regression with Random Effects", Statistics in Medicine, 17, pp. 2537-2550, 1998.*
Turner et al, "A Multilevel Model Framework for Meta-analysis of Clinical Trials with Binary Outcomes", Statistics in Medicine, 19, pp. 3417-3432.*
Minor, James M. et al., "Analysis of Clinical Data Using Neural Nets", J. Biopharmaceutical Statistics, 6(1), 83-104 (1996).
Hobbs et al., "FASTUS: A Cascaded Finite-State Transducer for Extracting Information form Natural-Language Text", http://www.ai.sri.com/natural-language/projects/fastus.html, not dated.
Marquardt, "An Algorithm for Least-Squares Estimation of Nonlinear Parameters", J Soc Indust Appl Math vol. II, No. 2, Jun. 1963 USA pp. 431-441.

(Continued)

*Primary Examiner*—Zoila Cabrera
*Assistant Examiner*—Mary C. Jacob

(57) ABSTRACT

Systems methods and recordable media for predicting multi-variable outcomes based on multi-variable inputs. Additionally, the models described can be used to predict the multi-variable inputs themselves, based on the multi-variable inputs, providing a smoothing function, acting as a noise filter. Both multi-variable inputs and multi-variable outputs may be simultaneously predicted, based upon the multi-variable inputs. The models find a critical subset of data points, or "tent poles" to optimally model all outcome variables simultaneously to leverage communalities among outcomes.

29 Claims, 12 Drawing Sheets

OTHER PUBLICATIONS

Diamantaras et al., *Principal Component Neural Networks, Theory and Applications* John Wiley & Sones, Inc., 1996, pp. 146-157.

Manning & Schutze, *Foundations of Statistical Natural Language Processing*, MIT Press, 1st ed., 1999, pp. xxix-xxxiii.

Minor et al., "Use of Neural Networks to Analyze Drug Combination Interactions", submitted to COMCON 4, 4th International Conference on Advances in Communication & Control Proceedings, 1993, pp. 504-515.

Minor et al., "Neural Net Methods for Mapping Thermodynamic and Physical Properties in Environmental Problems", Abstract submitted to 1996 AIChE Spring National Meeting, New Orleans, LA, Feb. 25-29, 1996.

Minor et al., "Competetive Advantage via Advanced Technology: Neural Networks and Quality Control", Abstract and Article submitted to 1995 Quality Control Conference, Santa Clara, CA, Apr. 4-7, 1995.

\* cited by examiner

300

|   | 240 | | | | | 340 | | | 440 | |
|---|---|---|---|---|---|---|---|---|---|---|
| Row | 1 | 2 | 3 | 4 ..... n | | 1 | 2 ..... M | | | Column |
| 1 | $X_{1,1}$ | $X_{1,2}$ | $X_{1,3}$ | $X_{1,4}$ ..... $X_{1,n}$ | | $Y_{1,1}$ | $Y_{1,2}$ ..... $Y_{1,M}$ | | $N_{0}1$ | |
| 2 | $X_{2,1}$ | $X_{2,2}$ | $X_{2,3}$ | $X_{2,4}$ ..... $X_{2,n}$ | | $Y_{2,1}$ | $Y_{2,2}$ ..... $Y_{2,M}$ | | $N_{0}2$ | |
| 3 | . | . | . | . . . . . . | | . | . . . . . . | | . | |
| 4 | . | . | . | . . . . . . | | . | . . . . . . | | . | |
| . | . | . | . | . . . . . . | | . | . . . . . . | | . | |
| N | $X_{N,1}$ | $X_{N,2}$ | $X_{N,3}$ | $X_{N,4}$ ..... $X_{N,n}$ | | $Y_{N,1}$ | $Y_{N,2}$ ..... $Y_{N,M}$ | | $N_{0}N$ | |

$$\mu_0^T \cdot \alpha = \begin{matrix} & \text{Row} \\ & 1 \\ & 2 \\ & 3 \\ & \cdot \\ & \cdot \\ & \cdot \\ & N \end{matrix} \begin{bmatrix} \mu_{0_1} \\ \mu_{0_2} \\ \mu_{0_3} \\ \cdot \\ \cdot \\ \cdot \\ \mu_{0_N} \end{bmatrix} \begin{bmatrix} \alpha_{0_{1,1}} & \alpha_{0_{1,2}} & \ldots & \alpha_{0_{1,M}} \end{bmatrix} = \overbrace{\begin{bmatrix} \text{Column} & 1 & 2 & \ldots & M \\ Y_{1,1} & Y_{1,2} & \cdot & \cdot & Y_{1,M} \\ \cdot & \cdot & \cdot & \cdot & \cdot \\ \cdot & \cdot & \cdot & \cdot & \cdot \\ \cdot & \cdot & \cdot & \cdot & \cdot \\ \cdot & \cdot & \cdot & \cdot & \cdot \\ Y_{N,1} & Y_{N,2} & \cdot & \cdot & Y_{N,M} \end{bmatrix}}^{340}$$

FIG. 7

$$\begin{bmatrix} \mu_{0_1} & S_{7,1} & S_{7,2} & S_{7,3} & S_{7,4} & S_{7,5} & S_{7,6} & S_{7,7} & \cdots \\ \mu_{0_2} & & & & & & & & \\ \mu_{0_3} & & & & & & & & \\ \vdots & & & & & & & & \\ \mu_{0_N} & & & & & & & & S_{7,N} \end{bmatrix} \begin{bmatrix} \alpha_{0_{1,1}} & \alpha_{0_{1,2}} & \cdots & \alpha_{0_{1,M}} \\ \alpha_{1_{2,1}} & \alpha_{1_{2,2}} & \cdots & \alpha_{1_{2,M}} \end{bmatrix} = \begin{bmatrix} Y_{1,1} & Y_{1,2} & \cdots & Y_{1,M} \\ \vdots & & & \vdots \\ Y_{N,1} & Y_{N,2} & \cdots & Y_{N,M} \end{bmatrix}$$

FIG. 8

$$T \rightarrow \begin{array}{c} \text{Row} \\ 1 \\ 2 \\ 3 \\ \vdots \\ N \\ N+1 \end{array} \begin{bmatrix} \begin{array}{cccccc} 1 & 2 & 3 & & & \\ \mu 0_1 & S_{7,1} & S_{3,1} & \cdots & & \\ \mu 0_2 & S_{7,2} & S_{3,2} & & & \\ \mu 0_3 & S_{7,3} & S_{3,3} & & & \\ \vdots & \vdots & \vdots & & & \\ \mu 0_N & S_{7,N} & S_{3,N} & & & \\ \mu 0_{N+1} & S_{7,N+1} & S_{3,N+1} & & & \end{array} \end{bmatrix} \begin{array}{c} \text{Column} \end{array}$$

$$\alpha \rightarrow \begin{bmatrix} \alpha 0_{1,1} & \alpha 0_{1,2} & \cdots & \alpha 0_{1,M} \\ \alpha 1_{2,1} & \alpha 1_{2,2} & \cdots & \alpha 1_{2,M} \\ \alpha 2_{3,1} & \alpha 2_{3,2} & \cdots & \alpha 2_{3,M} \end{bmatrix}$$

$$= \underbrace{\begin{bmatrix} \begin{array}{cccc} 1 & 2 & \cdots & M \\ Y_{1,1} & Y_{1,2} & \cdots & Y_{1,M} \\ Y_{2,1} & Y_{2,2} & \cdots & Y_{2,M} \\ \vdots & \vdots & & \vdots \\ Y_{N,1} & Y_{N,2} & \cdots & Y_{N,M} \\ Y_{N+1,1} & Y_{N+1,2} & \cdots & Y_{N+1,M} \end{array} \end{bmatrix}}_{340} \begin{array}{c} \text{Column} \end{array}$$

METHOD AND SYSTEM FOR PREDICTING MULTI-VARIABLE OUTCOMES

CROSS-REFERENCE

This application claims the benefit of U.S. Provisional Application No. 60/368,586, filed Mar. 29, 2002, which application is incorporated herein, in its entirety, by reference thereto.

FIELD OF THE INVENTION

The present invention relates to software, methods, and devices for evaluating correlations between observed phenomena and one or more factors having putative statistical relationships with such observed phenomena. More particularly, the software, methods, and devices described herein relate to the prediction of the suitability of new compounds for drug development, including predictions for diagnosis, efficacy, toxicity, and compound similarity among others. The present invention may also be applicable in making predictions relating to other complex, multivariate fields, including earthquake predictions, economic predictions, and others. For example the transmission of seismic signals through a particular fault may exhibit significant changes in properties prior to fault shifting. One could use the seismic transmissions of the many small faults that are always active near major fault lines.

BACKGROUND OF THE INVENTION

The application of statistical methods to the treatment of disease, through drug therapy, for example, provides valuable tools to researchers and practitioners for effective treatment methodologies based not only on the treatment regimen, but taking into account the patient profile as well. Using statistical methodologies, physicians and research scientists have been able to identify sources, behaviors, and treatments for a wide variety of illnesses. Thus, for example, in the developed world, diseases such as cholera have been virtually eliminated due in great part to the understanding of the causes of, and treatments for, these diseases using statistical analysis of the various risk and treatment factors associated with these diseases.

The most widely used statistical methods currently used in the medical and drug discovery fields are generally limited to conventional regression methods which relate clinical variables obtained from patients being treated for a disease with the probable treatment outcomes for those patients, based upon data relating to the particular drug, drugs or treatment methodology being performed on that patient. For example, logistic regression methods are used to estimate the probability of defined outcomes as impacted by associated information. Typically, these methods utilize a sigmoidal logistic probability function that is used to model the treatment outcome. The values of the model's parameters are determined using maximum likelihood estimation methods. The non-linearity of the parameters in the logistic probability function, coupled with the use of the maximum likelihood estimation procedure, makes logistic regression methods complicated. Thus, such methods are often ineffective for complex models in which interactions among the various clinical variables being studied are present, or where multivariable characterizations of the outcomes are desired, such as when characterizing an experimental drug. In addition, the coupling of logistic and maximum likelihood methods limits the validation of logistic models to retrospective predictions that can overestimate the model's true abilities.

Such conventional regression models can be combined with discriminant analysis to consider the relationships among the clinical variables being studied to provide a linear statistical model that is effective to discriminate among patient categories (e.g., responder and non-responder). Often these models comprise multivariate products of the clinical data being studied and utilize modifications of the methods commonly used in the purely regression-based models. In addition, the combined regression/discriminant models can be validated using prospective statistical methods in addition to retrospective statistical methods to provide a more accurate assessment of the model's predictive capability. However, these combined models are effective only for limited degrees of interactions among clinical variables and thus are inadequate for many applications.

The Similarity Least Square Modeling Method (SMILES) disclosed in U.S. Pat. No. 5,860,917 (of which the present inventor is a co-inventor), and which is hereby incorporated, in its entirety, by reference thereto, is capable of predicting an outcome (Y) as a function of a profile (X) of related measurements and observations based on a viable definition of similarity between such profiles. SMILES fails, however, to provide a means to effectively handle multiple outcome variables or outcomes of different types. For multiple outcome variables, or Y-variables, SMILES analyzes each Y-variable separately as independent measurements or observations. Thus, one obtains a separate model for each Y-variable. When the Y-variables measure the same phenomena, they likely have induced interdependencies or communalities. It becomes difficult to perform analysis with separate independent models. Nuisance and noise factors complicate this task even further.

What is needed, therefore, are methods of providing statistically meaningful models for analyzing the Y-variables as an ensemble of related observations, to produce a a common model for all Y-variables as a function of multiple X-variables to obtain a more efficient model with better leverage on common phenomena and less noise.

SUMMARY OF THE INVENTION

The present invention includes systems, methods and recordable media for predicting multi-variable outcomes based on multi-variable inputs. In one aspect of the invention, a predictor model is generated by: a) defining an initial model as Model Zero and inputting Model Zero as initial column(s) one or more of a similarity matrix T; b) performing an optimization procedure (e.g., least squares regression or other linear regression procedure, non-linear regression procedure, maximum entropy procedure, mini-max entropy procedure or other optimization procedure) to solve for matrix values of an $\alpha$ matrix which is a transformation of outcome profiles associated with input profiles; c) calculating a residual matrix c based on the difference between the actual outcome values and the predicted outcome values determined through a product of matrix T and matrix $\alpha$, d) selecting a row of the a residual matrix $\epsilon$ which contains an error value most closely matching a pre-defined error criterion; e) identifying a row from a matrix of the multivariable inputs which corresponds to the selected row from the residual matrix $\epsilon$; f) calculating similarity values between the identified row and each of the rows in the matrix of the multivariable inputs, including the identified row with itself; g) populating the next column of similarity matrix T with the calculated similarity values if it is determined that such column of the identified row is not collinear or nearly collinear with Model Zero and columns of previously identified rows, the similarity values for which were used to populate such previous columns of similarity matrix T; and h) repeating steps b) through g) until a predefined stopping criterion has been reached.

In another aspect of the present invention, the predictor model may be used to predict multi-variable outcomes for multi-variable income data of which the outcomes are not known.

In another aspect of the present invention, the model learns to represent a process from process profile data such as process input, process output, process parameters, process controls and/or process metrics, so that the trained model is useful for process optimization, model-based process control, statistical process control and/or quality assurance and control.

In another aspect of the present invention, a model may be used to self-predict multi-variable profiles, wherein the input multivariable profiles are used to predict the input multi-variable profiles themselves as multi-variable outputs.

In another aspect of the present invention, the self-prediction model is used iteratively to impute data values to missing data values in the multivariable input profiles.

In another aspect of the present invention, a model is used to simultaneously predict both multi-variable X-input profiles and multi variable Y-output profiles based on the multi-variable X-input profiles.

In another aspect Y-columns may be similarity values of a select subset of the original Y-variables by analogy to S-columns as similarity values of the X-variables.

In another aspect of the present invention, score functions may be optimally assigned to the predicted multi-variable outcomes for use in any multivariate distribution process, such as ordinal, logistic, and survival probability analysis and predictions.

In yet another aspect, the identified rows, also described as math-functional "tent pole" locations, may be tested for ellipticity as a function of the X-space, using the Marquardt-Levenberg algorithm, and then ranked according to the testing.

Still further, the present invention may include determining one or more decay constants for each of the identified rows of X-profiles (tent pole locations) used to calculate similarity values to populate the T matrix (similarity matrix).

Methods, systems and recordable media are disclosed for generating a predictor model for predicting multivariable outcomes (a matrix of rows of Y-profiles) based upon multivariable inputs (a matrix of rows of X-profiles) with consideration of nuisance or noise variables, by analyzing each X-profile row of multivariable inputs as an object; calculating similarity among the objects; selecting tent pole locations determined to be critical profiles in supporting a prediction function for predicting the Y-profiles; determining a maximum number of such profiles by model properties such as collinearity or max fit error or least squares sum of squared errors; and optimizing the final number of tent poles by prospective "true" prediction properties such as the minimum of the sum of squared "prospective errors or ensemble errors" between the Y-profile predictions and the know Y-profile value(s).

According to the present invention, the dimensions of the data can be reduced to a lower dimension as defined only by necessary critical components to represent the phenomenon being modeled. Hence, in general, the present invention is valuable to help researchers "see" the high-dimensional patterns from limited noisy data on complex phenomenon that can involve multiple inputs and multiple consequential outputs (e.g., outcomes or responses).

The present invention can optimize the model fit and/or the model predictions and provides diagnostics that measure the predictive and fit capabilities of a derived model. Input profile components may simultaneously be included as outcome variables and vice versa, thus enabling a nonlinear version of partial least squares that induces proper matrix-eigenvalue matching between input and output matrices. Eigenvalue matching is well-practiced as linear transformations related to generalized singular value decompositions (GSVD). The present invention can also be used for self-prediction imputation and smoothing, e.g., predicting smoothed and missing values in input data based on key profiles in the input data.

The present invention includes the capability to measure the relative importance of individual input variables to the prediction and fit process by nonlinear statistical parameters calculated by the Marquardt-Levenberg algorithm. The present invention can also associate decay constants with each location (tent poles) which is useful to quantify types and scopes of the influence of that profile on the model, i.e., local and/or global effect.

The present invention finds a critical subset of data points to optimally model all outcome variables simultaneously to leverage both communalities among outcomes and uniqueness properties of each outcome. The method relates measured variables associated with a complex phenomenon using a simple direct functional process that eliminates artifactual inferences even if the data is sparse or limited and the variable space is high dimensional. The present invention can also be layered to model higher-ordered features, e.g., output of a GSMILES network can be input to a second GSMILES network. Such GSMILES networks may include feedback loops. If profiles include one or more ordered indices such as "time," GSMILES networks can incorporate the ordering of such indices (i.e., "time" series). GSMILES also provides statistical evaluations and diagnostics of the analysis, both retrospective and prospective scenarios. GSMILES reduces random noise by combining data from replicate and nearby adjacent information (i.e., pseudo-replicates).

BRIEF DESCRIPTION OF THE DRAWINGS

FIG. 3 is an example matrix containing a training set of X-profiles, Y-profiles, and a noise or nuisance profile used by GMILES in forming a predictor inference model. Such nuisance profile can represent many variables, i.e., a vector of noise factors usually with specifics unknown.

FIG. 5 illustrates an example of an initial model (Model Zero) used to solve for the critical profiles, in the example shown, the first critical profile or tent poles is being solved for.

FIG. 7 shows a second iteration, following the example of FIGS. 5 and 6, used to solve for the second tent pole.

FIG. 8 shows an example of a test X-profile being inputted to GSMILES in order to predict a Y-Profile for the same.

DETAILED DESCRIPTION OF THE INVENTION

Figure 1:
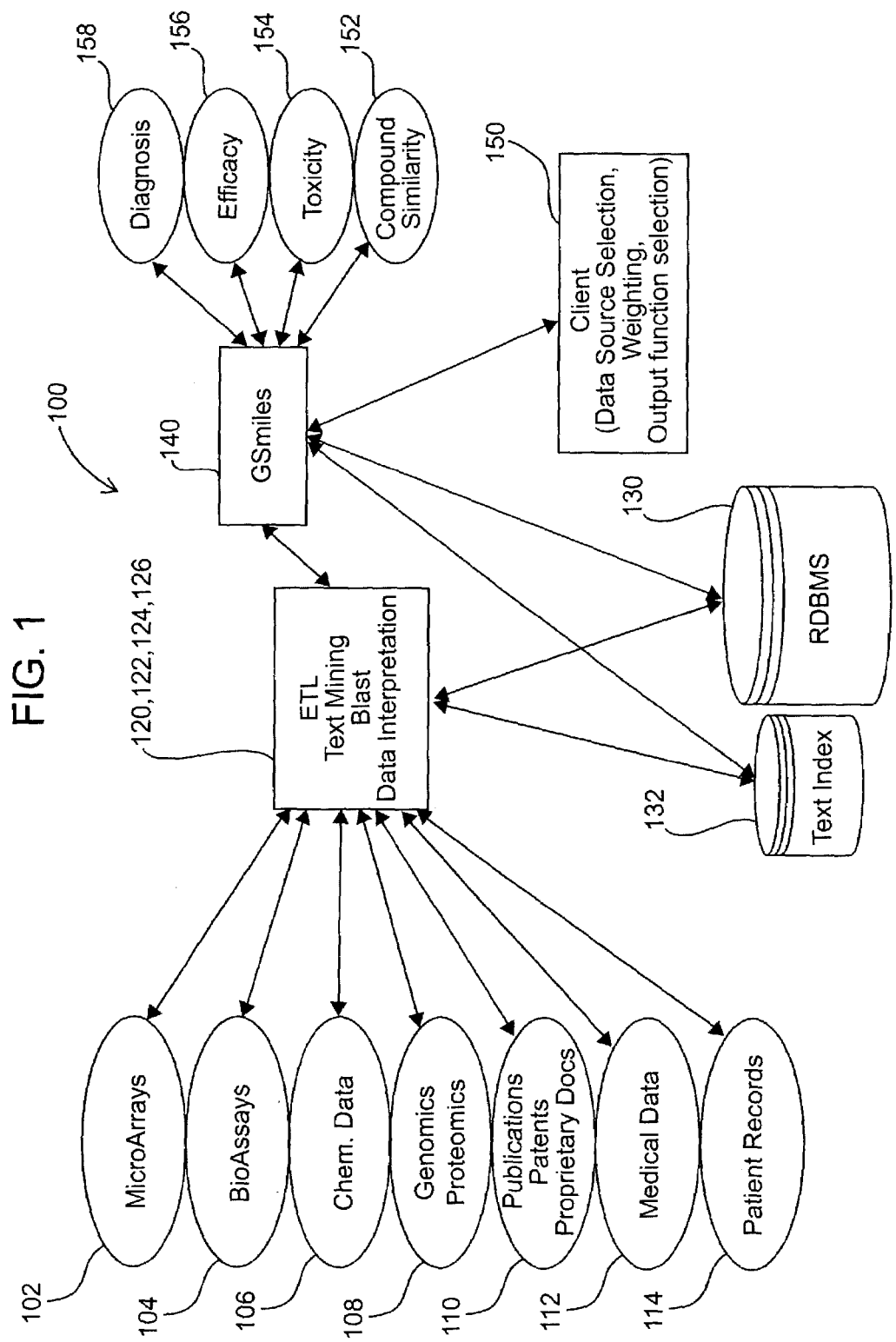
FIG. 1 is an architecture diagram showing examples of input sources that may supply data to the predictor system according to the present invention.

Before the present invention is described, it is to be understood that this invention is not limited to particular statistical methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and systems similar or equivalent to those described herein can be used in the practice or testing of the present invention, the preferred methods and systems are now described. All publications mentioned herein are incorporated herein by reference to disclose and describe the methods and/or systems in connection with which the publications are cited.

It must be noted that as used herein and in the appended claims, the singular forms "a", "and", and "the" include plural referents unless the context clearly dictates otherwise.

Thus, for example, reference to "a variable" includes a plurality of such variables and reference to "the column" includes reference to one or more columns and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

"Microarrays" measure the degree to which genes are expressed in a particular cell or tissue. One-channel microarrays attempt to estimate an absolute measure of expression. Two-channel microarrays compare two different cell types or tissues and output a measure of relative strength of expression.

"RTPCR" designates Real Time Polymerized Chain Reaction, and includes techniques such as Taqman™, for example, for high resolution gene expression profiling.

"Bioassays" are experiments that determined properties of biological systems and measure certain quantities. Microarrays are an example of bioassays. Other bioassays are fluorescence assays (which cause a cell to fluoresce if a certain biological event occurs) and yeast two-hybrids (which determine whether two proteins of interest bind to each other or not).

"Chemical data" include the chemical structure of compounds, chemical and physical properties of compounds (such as solubility, pH value, viscosity, etc.), and properties of compounds that are of interest in pharmacology, e.g., toxicity for particular tissues in particular species, etc.

"Process control" includes all methods such as feed-forward, feed-backward, and model-based control loops and policies used to stabilize, reduce noise, and/or control any process (e.g., production lines in factories), based on inherent correlations between systematic components and noise components of the process.

"Statistical process control" refers to statistical evaluation of process parameters and/or process-product parameters to verify process stability and/or product quality based on non-correlated noise.

"Genomics databases" contain nucleotide sequences. Nucleotide sequences include DNA (the information in the nucleus of eukaryotes that is propagated in cell division and is the basis for transcription), messenger RNA (the transcripts that are then translated into proteins), and ribosomal and transfer RNA (part of the translation machinery).

"Proteomics databases" contain amino acid sequences, both sequences inferred from genomic data and sequences found through various bioassays and experiments that reveal the sequences of proteins and peptides.

"Publications" include medline (the collection of biomedical abstracts distributed by the national library of medicine), biomedical journals, journal articles from related fields, such as chemistry and ecology, or articles, books or any other published material in the field being examined, whether it be geology, economics, etc.

"Patent" includes U.S. patents and patents throughout the world, as well as pending patent applications that are published.

"Proprietary documents" include those documents which have not been published, or are not intended to be published.

"Medical data" include all data that are generated by diagnostic devices, such as urinalysis, blood tests, and data generated by devices that are currently under investigation for their diagnostic potential (e.g., microarrays, mass spectroscopy data, etc.).

"Patient records" are the records that physicians and nurses maintain to record a patient's medical history. Increasingly, information is captured electronically as a patient interacts with hospitals and practitioners. Any textual data captured electronically in this context may be part of patient records.

When one location is indicated as being "remote" form another, this refers to the tow locations which are at least in different buildings, and these locations may be at least one mile, ten miles or at least one hundred miles apart.

"Transmitting" information refers to sending the data representing that information as electrical signals over a suitable communication channel (e.g., a private or public network).

"Forwarding" a result refers to any means of getting that result from one location to the next, whether by transmitting data representing the result or physically transporting a medium carrying the data or communicating the data.

A "result" obtained from a method of the present invention includes one directly or indirectly obtained from use of the present invention. For example, a directly obtained "result" may include a predictor model generated using the present invention. An indirectly obtained "result" may include a clinical diagnosis, treatment recommendation, or a prediction of patient response to a treatment which was made using a predictor model which was generated by the present invention.

The present invention provides methods and systems for extracting meaningful information from the rapidly growing amount of genomic and clinical data, using sophisticated statistical algorithms and natural language processing. The block diagram in FIG. 1 illustrates an exemplary architecture of a predictor system 100 according to one embodiment of the present invention. The predictor system 100 takes input from various sources (such as microarrays 102, bioassays 104, chemical data 106, genomics/proteomics 108, publications/patents/proprietary documentation 110, medical data 112, and patient records 114, (as indicated in FIG. 1) and preprocesses the input using one or more of the ETL (Extraction/Transformation/Loading module, a standard data mining module for getting the data into a format you can work with) 120, text mining 122, Blast 124, and data interpretation 126 modules.

The ETL module 120 extracts data relating to one or more entities (e.g., compounds) from a data source. The extracted data correspond to input and output variables to be used in the GSMILES model for the particular compound. Examples of data extraction and manipulation tasks supported by the ETL module include XML parsing; recognizing various columns and row delimiters in unstructured files; and automatic recognition of the structure of a file (e.g., XML, unstructured, or some other data exchange format).

Once the ETL module extracts the data, it may transform the data with simple preprocessing steps. For example, the ETL module may normalize the data and filter out noise and non-relevant data points. The ETL module then loads the data into the RDBMS (i.e., relational database management system) in a form that is usable in the GSMILES process, e.g., the input and output variables according to the GSMILES model. Specifically, the ETL module loads the extracted (and preferably preprocessed) data into the RDBMS in fields corresponding to the input and output variables for the entities to which the data relate.

The ETL module may be run in two modes. If a data source is available permanently, data are processed in batch mode and stored in the RDBMS. If a data source is interactively supplied by the user, it will be processed interactively by the ETL module.

The text mining module 122 processes textual input from sources such as publications 110 and patient records 114. Text mining module 122 produces two types of outputs: structured output stored in the database 130, and unstructured keyword vectors stored in an inverted index (Text Index) 132. Unlike a conventional inverted index, Text Index 132 also preferably functions to retrieve pre-computed keyword vectors. This is important for text types such as patient records.

In one embodiment, text mining module 122 includes three components: a term matching component (including specialized dictionaries and regular expression parsers for mapping text strings to entities in an underlying ontology); a relationship mapping component (including patterns that occur in general language as well as patterns that are specific to the domain) for recognizing relationships between entities in text (such as drug-protein interactions and gene-disease causal relationships); and a learning component which learns terms and relationships based on an initial set of terms and relationships supplied by a domain expert.

In one embodiment, text mining module 122 uses techniques taught by the FASTUS (Finite State Automaton Text Understanding System) System, developed by SRI International, Menlo Park, Calif. These techniques are described in Hobbs et al., "FASTUS: A Cascaded Finite-State Transducer for Extracting Information form Natural-Language Text", which can be found at the natural language projects web page of SRI, and which is incorporated herein, in its entirety, by reference thereto. Text mining techniques are well-known in the art, and a comprehensive discussion thereof can be found in the textbook by Christopher D. Manning & Hinrich Schutze, Foundations of Statistical Natural Language Processing (MIT Press: 1st ed., 1999).

The Blast or Homology module 124 detects sequence data in data sources (e.g., microarrays 102, patents 110, patient records 114, etc.), and stores them in a unified format such as FASTA The Homology module 124 uses BLAST or other known sequence identification methods. Homology module 124 is called interactively for sequence similarity computation by GSMILES 140 (if sequence similarity is part of the overall similarity between data points computed).

Data interpretation module 126 performs a number of tasks that go beyond the more mechanical processing done by ETL module 120. One of the tasks performed by data interpretation module 126 is that of imputation, where missing data are filled in, where possible, using GSMILES processing. Another function of data interpretation module is data linkage. If the same data type occurs in several sources, but under different names, then data interpretation module 126 reconciles the apparent disparity offered by the different names, by linking these terms (e.g., such as when different naming conventions are used for drugs or genes).

Client 150 allows a user to interact with the system 100. In data source selection, the user selects which data sources are most important for a particular prediction task. If a new data source has become available, the user may add the new data source to the system 100. Weighting may be employed to determine the relative significance, or weight, of various data sources. For example, if a user has prior knowledge indicating that most of the predictive power comes from microarrays for a particular classification task, then the user would indicate this with a large weighting factor applied to the microarrays data source.

The client 150 performs output function selection when the user selects one or more particular output categories of interest (i.e., the response variables). When a response variable is used for the first time, the user needs to make it accessible to the system and configure it (e.g., the user determines what kind of response variable it is, such as continuous, dichotomous, polytomous, etc.).

By processing the preprocessed data received from ETL 120, text mining 122, Blast 124 and/or data interpretation 126 modules to arrive at predictive values according to the selected output function or functions, GSMILES 140 may provide valuable predictive information as to compound similarities 152, toxicity 154, efficacy 156, and diagnosis 158, but is not limited to such output functions, as has been noted earlier.

Information may be exchanged with Text Index 132.

Module(s) 120,122,124 and/or 126 exchange(s) data with RDBMS 130 and/or Text Index 132, as described above. The preprocessed data from module(s) 120,122,124 and/or 126 are fed into GSMILES (Generalized Similarity Least Squares Modeling Method) predictor module 140, which again exchanges data with Text Index 132 and RDBMS 130, but also takes input from client 150, for example, as to data source selection, weighting of data points, and output function selection. The output from GSMILES 140 may include predictions for various compounds of diagnosis, efficacy, toxicity, and compound similarity, among others.

One important aspect of the methods and systems disclosed concerns their use in the prediction of the suitability of new compounds for drug development. GSMILES predictor 140 may predict various aspects of a compound, such as toxicity, mode of action, indication and drug success, as well as consideration of similar compounds, while accepting user input to the various corresponding models. The sum of all the prediction results can be used at the end to decide which compound to pursue. By predicting a compound's mode of action, toxicology, and other attributes, the present invention facilitates lead prioritization and helps design experiments.

The present system may utilize the Generalized Similarity Least Squares (GSMILES) modeling method to reveal association patterns within genomic, proteomic, clinical, and chemical information and predict related outcomes such as disease state, response to therapy, survival time, toxic events, genomic properties, immune response/rejection level, and measures of kinetics/efficacy of single or multiple therapeutics. The GSMILES methodology performed by GSMILES module 140 is further discussed in the next section. Other possible applications of GSMILES include economic predictions, early detection of critical earthquake-related processes from appropriately filtered seismic signals and other geophysical measurements, and process models for process control of complex chemical processes to improve efficiency and protect the environment.

The GSMILES Methodology

A useful method and system for extracting meaningful information from the genomic and clinical data requires an efficient algorithm, an effective model, helpful diagnostic measures and, most importantly, the capability to handle multiple outcomes and outcomes of different types. The ability to handle multiple outcomes and outcomes of different types is necessary for many types of complex modeling.

For example, genomic and clinical data are typically represented as related series of data values or profiles, requiring a multi-variate analysis of outcomes.

The Similarity Least Square Modeling Method (SMILES) disclosed in U.S. Pat. No. 5,860,917 (of which the present inventor is a co-inventor, and which was incorporated by reference above), is capable of predicting an outcome (Y) as a function of a profile (X) of related measurements and observations based on a viable definition of similarity between such profiles. SMILES fails, however, to provide a means to effectively handle multiple outcome variables or outcomes of different types. For multiple outcome variables, or Y-variables, SMILES analyzes each Y-variable separately as independent measurements or observations. Thus, one obtains a separate model for each Y-variable. When the Y-variables measure the same phenomena, they likely have induced interdependencies or communalities. It becomes difficult to perform analysis with separate independent models. Nuisance and noise factors complicate this task even further.

GSMILES remedies this deficiency by analyzing the Y-variables as an ensemble of related observations. GSMILES produces a common model for all Y-variables as a function of multiple X-variables to obtain a more efficient model with better leverage on common phenomena with less noise. This aspect of GSMILES allows a user to find strategic gene compound associations that involve multiple-X/multiple-Y variables on noisy cell functions or responses to stimuli.

GSMILES treats each profile of associated measurements of variables as an object with three classes of information: predictor/driver variables (X-variables), predictee/consequential variables (Y-variables), and nuisance variables (noise variables, known and unknown). Note that these classes are not mutually exclusive; hence, a variable can belong to one or more of such GSMILES classes as dictated by each application.

GSMILES calculates similarity among all such objects using a definition of similarity based on the X-variables. Note that similarity may be compound, e.g., a combination of similarity measures, where each similarity component is specific to a subset of profile X-variables. GSMILES uses such similarity values to predict the Y-variables. It selects a critical subset of objects that can optimally predict the Y-values of all objects within the precision limitations imposed by nuisance effects, assured by statistically valid criteria. An iterative algorithm as discussed below may make the selection.

Figure 2:
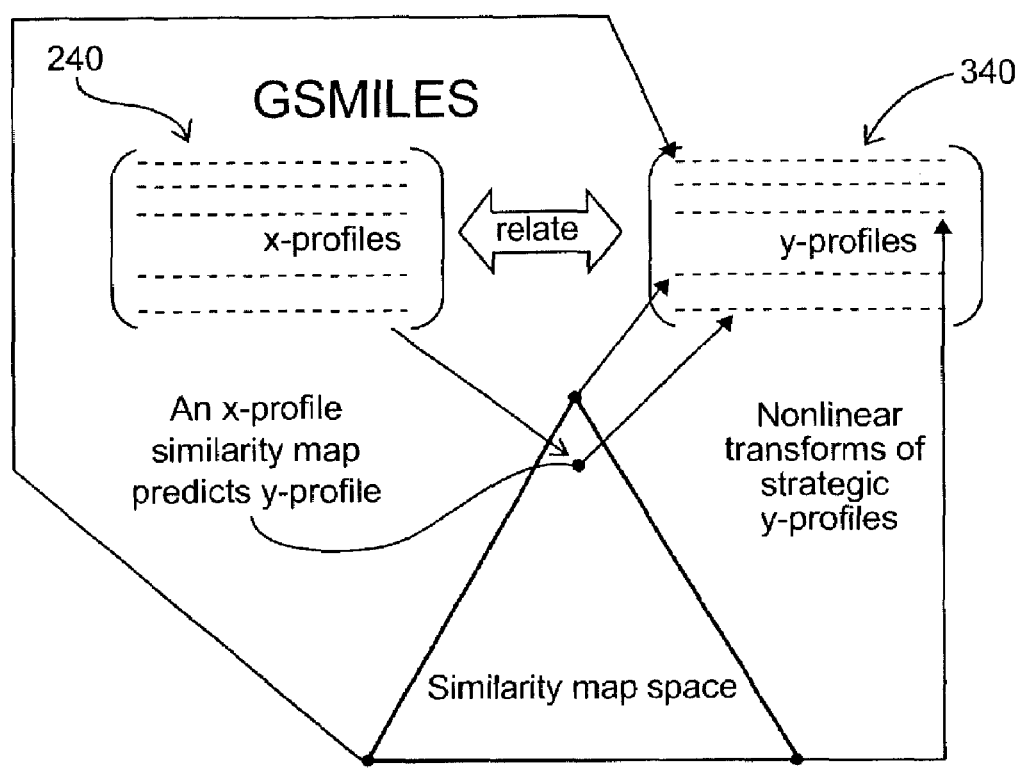
FIG. 2 is a schematic diagram illustrating the ability of GSMILES to relate Y-profiles to X-profiles through an X-profile similarity map that performs nonlinear-X transforms of strategic Y-profiles. The similarity matrix assuming no Model Zero (i.e., null Model Zero) is renormalized so that each row becomes a vector of convex coefficients, i.e., whose sum equals one with each coefficient in interval [0,1].

Affine prospective predictions of Y-profiles may be performed to predict profiles (i.e., row vectors) in the Y-outcome-variable matrix 340 using matched profiles in X-input-variable matrix 240, see FIG. 2. For simplicity, assume use of a null Model Zero. GSMILES 140 processes the function:

$$Z = SR \tag{1}$$

where Z is an N×M matrix of predicted Y values (where N and M are positive integers);

S is an N×P matrix of similarity values between profiles in matrix X (where N and P are positive integers, which may further include one or more columns of Model Zero values, as will be discussed below); and R is an X-nonlinear transformation of P Y-profiles associated with P strategic X profiles (also referred to as "α" values, below).

The final prediction model according to this methodology is prospective, since each predicted row of Y in turn is used to estimate a prospective error, the sum of squares of which determine the optimal number of model terms by minimization. The transforms are optimized to minimize the least-squares error between Z and Y. Thus, R is a P×M matrix of P optimal transforms of Y-profiles and the similarity values in each row of S are the strategic affine coefficients for these optimal profiles to predict the associated row in Y. In this way, GSMILES not only represents Y efficiently, but reduces noise by functional smoothing.

Equation (1) can be easily transformed into a mixture representation by normalizing each row of S to sum to unity as follows:

$$DZ=DSR \qquad (2)$$

where D is a diagonal matrix of the inverse of the sum or each row of matrix S.

The GSMILES methodology finds the strategic locations in matrix X 240 and determines p to optimize the prospective representation of the Y-profiles 340, including optimization of relationships within the Y-profiles.

Referring to FIG. 3, GSMILES arranges the X-profile and Y-profile, and also a noise profile 440 in a matrix 300. Noises are like hidden variables. Noises are ever present but it is not known how to extract the values of these variables. All inference models must accommodate noise. Each row of matrix 300 represents a series of values for related variables, e.g., the X-values for row 1 of the matrix could be known, measured, or inputted values (or may even be dummy variables) which directly effect the Y-values of row 1, which can be thought of as output or outcome values, and wherein the $N_0$-values (noise) represent the noise values associated with each row. The left-side 240 of the rows of matrix 300, which are populated by the X variables in FIG. 3 define the X-profile of the problem and the right-side (340, 440) of the rows of matrix 300, which are populated by the Y and $N_0$ variables in FIG. 3 define the Y-profile and noise associated with the rows.

Each row of matrix 300 may be treated as a data object, i.e., an encapsulation of related information. The GSMILES methodology analyzes these objects and compares them with some measure of similarity (or dissimilarity). A fundamental underlying assumption of the GSMILES methodology is that if the X values are close in similarity, then the Y-values associated with those rows will also be close in value. By processing the objects in the matrix 300, a similarity transform matrix may be constructed using similarity values between selected rows of the X-profile, as will be described in more detail below. The X-profile objects (rows) are used to determine similarity among one another to produce similarity values used in the similarity transform matrix. Similarity between rows may be calculated by many different known similarity algorithms, including, but not limited to Euclidean distance, Hamming distance, Minkowski weighted distance, or other known distance measurement algorithms. The normalized Hamming function measures the number of bits that are dissimilar in two binary sets. The Tanimoto or Jaccard coefficient measures the number of bits shared by two molecules relative to the ones they could have in common. The Dice coefficient may also be used, as well as similarity metrics between images or signal signatures when the input contains images or other signal patterns, as known to those of ordinary skill in the art.

With any set of data being analyzed, such as the data in matrix 300, for example, it has been found that certain, select X-profiles among the objects are more critical in defining the relationship of the function sought than are the remainder of the X-profiles. GSMILES solves for these critical profiles that give critical information about the relationship between the X values and the Y values.

Figure 4:
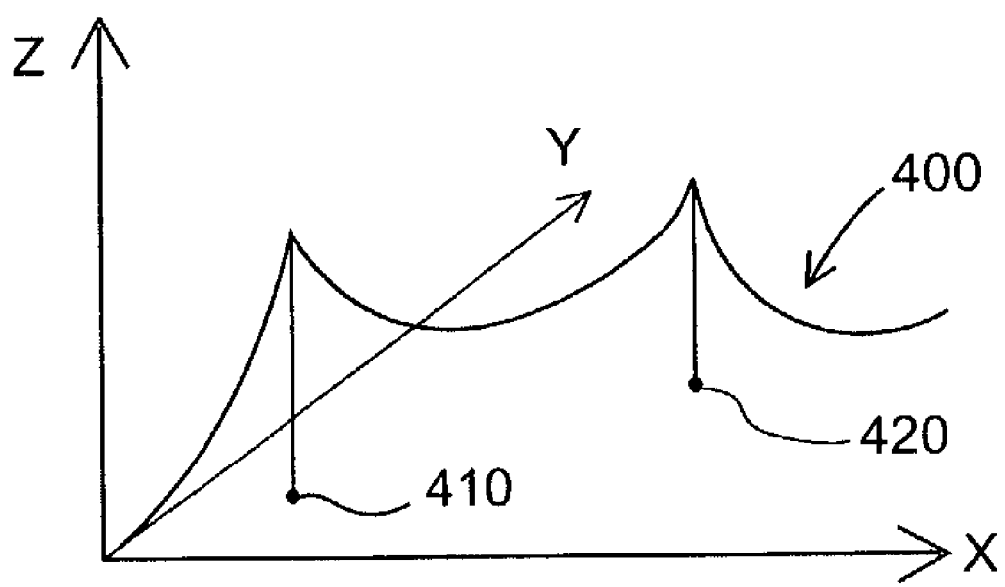
FIG. 4 is a diagram of a function 400 shown in a three-dimensional space, illustrating support locations along the function that can be "supported" by critical values (or profiles, i.e., the locations for the alpha coefficients representing the size and direction of the "tent pole") in the X-Y space.

Conceptually speaking, if a function 400 is observed in a three-dimensional space, as shown in FIG. 4, there are certain domain locations of the function identifying features that can be "supported" by nearby critical data values (or profiles) in the X-Y space. For example, the points 410 and 420 in FIG. 4 are such critical values in the X-Y space. When these locations become the centroids of support for the range of the function, as facilitated by similarity functions, they tend to adequately support the total surface shape of the range of the function. Because of the appearance of this conceptual model, where the function range appears somewhat like a circus tent, and the critical domain locations, together with their extended impact, appear as tent poles, the present inventors refer to the critical profiles as "tent poles". Of course these "tent poles" can be positive or negative as applied to a mathematical function. This same concept applies to high dimensional problems and functions. GSMILES calculates the critical profiles, which define the locations of the "tent poles", as well as their optimized coefficients (i.e., length or size of the tent poles).

To solve for the critical profiles, an initial model (called Model Zero (Model 0) is inputted to the system, in matrix T (See FIG. 5). Model Zero (designated as $\mu_0$ in FIG. 5), may be a conventional model, conceptual model, theoretical model, and X-profile with known Y-profile outcomes, or some other reasonable model which characterizes a rough approximation of the association between the X- and Y-profiles, but still cannot explain or account for a lot of systematic patterns effecting the problem. Thus, Model Zero predicts Y (i.e., the Y values in the Y-profile), but not adequately. Alternatively, a null set could be used as Model Zero, or a column of equal constants, such as a column with each row in the column being the value 1 (one).

A least squares regression algorithm is next performed to solve for coefficients $\alpha_0$ (see matrix $\alpha$, FIG. 5) which will provide a best fit for the use of Model zero to predict the Y-profiles, based on the known quantities in matrix $\mu_0$ and matrix 340. It should be noted here that this step of the present invention is not limited to solving by least squares regression. Other linear regression procedures, such as median regression, ordinal regression, distributional regression, survival regression, or other known linear regression techniques may be utilized. Still further, non-linear regression procedures, maximum entropy procedures, mini-max entropy procedures or other optimization procedures may be employed. Solving for the $\alpha_0$ matrix $\alpha$ optimizes Model Zero to predict the Y-profile 340. Then the prediction errors (residuals) are calculated as follows:

$$Y-(T\cdot\alpha)=\epsilon \qquad (3)$$

where $Y$=matrix 340;

$\alpha$=$\alpha$ matrix (which is a 1×M vector in the example shown in FIG. 5);

$T$=the T matrix (i.e., vector, in this example, although the Model Zero profile may be a matrix having more than one column); and $\epsilon$=error matrix, or residuals, in this example characterizing Model Zero with $\epsilon_0$ values.

Figure 6:
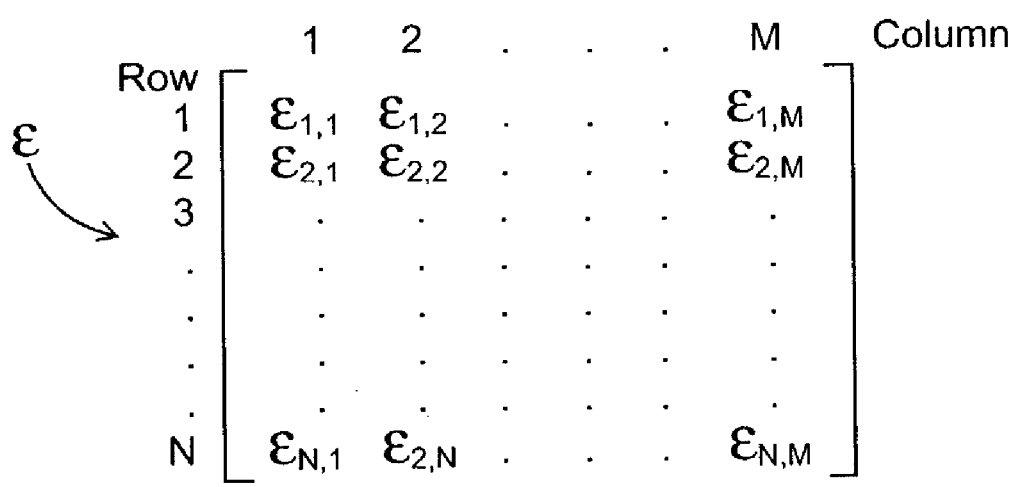
FIG. 6 shows the error matrix resulting from processing, using the example shown in FIG. 5.

The error matrix e resulting from processing, using the example shown in FIG. 5 is shown in FIG. 6. Next, GSMILES determines the row of the $\epsilon$ matrix which has the maximum absolute value of error. Note that for problems where the Y-profile is a vector (i.e., an N×1 matrix, i.e., where M=1), the error matrix $\epsilon$ will be a vector (i.e., an N×1 matrix) and the maximum absolute error can be easily determined by simply picking the largest absolute value in the error vector. For the example shown in FIG. 5, however, the error matrix $\epsilon$ is an N×M matrix, as shown in FIG. 6. To determine maximum values in a matrix of error values, such as matrix $\epsilon$, different options are available. The simplest approach, while not necessarily achieving the best results of all the approaches, is to simply pick the maximum absolute error value from the entire set of values displayed in matrix $\epsilon$. Another approach is to construct an ensemble error for each row of error values in matrix $\epsilon$. One way of constructing the ensemble errors is to calculate an average error for each entire row. This results in an error vector, from which the maximum absolute error can be chosen.

Whatever technique is used to determine the maximum absolute error, the row from which the maximum absolute error is noted and used to identify the row (X-profile) from matrix 240, from which similarity values are calculated. The calculated similarity values are used to populate the next column of values in the matrix containing Model Zero. For example, at this stage of the processing, the similarity values will be used to populate the second column of the matrix, adjacent the Model Zero values. However, this is an iterative process which can be used to populate as many columns as necessary to produce a "good or adequate fit", i.e., to refine the model so that it predicts Y-profiles within acceptable error ranges. An acceptable error range will vary depending upon the particular problem that is being studied, and the nature of the Y-profiles. For example, a model to predict temperatures may require predictions within an error range of ±1° C. for one application, while another application for predicting temperature may require predictions within an error range of ±0.01° C. GSMILES is readily adaptable to customize a model to meet the required accuracy of the predictions that it produces.

Assuming, for exemplary purposes, that the row from which the maximum absolute error was found in matrix E was the seventh, GSMILES then identifies the seventh row in matrix 240 to perform the similarity calculations from. Similarity calculations are performed between the seventh X-profile and each of the other X-profile rows, including the seventh row X-profile with itself. For example, the first row similarity value in column 2, FIG. 7 (i.e., $S_{7,1}$) is populated with the similarity value calculated between rows 7 and 1 of the X-profile matrix 240. The second row similarity value in column 2, FIG. 7 is populated with the similarity value $S_{7,2}$, the similarity value calculated between rows 7 and 2, and so forth. Note that row 7 is populated with a similarity value calculated between row 7 with itself. This will be the maximum similarity value, as a row is most similar with itself and any replicate rows. The similarity values may be normalized so that the maximum similarity value is assigned a value of 1 (one) and the least similar value would in that case be zero. As noted, row 7 was only chosen as an example, but analogous calculations would be performed with regard to any row in the matrix 240 which was identified as corresponding to the highest maximum absolute error value, as would be apparent to those of ordinary skill in the art. It is further noted that selection does not have to be based upon the maximum absolute error value, but may be based on any predefined ensemble error scoring. For example, an ensemble average absolute error, ensemble median absolute error, ensemble mode absolute error, ensemble weighted average absolute error, ensemble robust average absolute error, geometric average, ensemble error divided by standard deviation of errors of ensemble, or other predefined absolute error measure may be used in place of the maximum absolute error or maximum ensemble absolute error.

The X-profile row selected for calculating the similarity values marks the location of the first critical profile or "tent pole" identified by GSMILES for the model. A least squares regression algorithm is again performed next, this time to solve for coefficients $\alpha_0$ and $\alpha_1$ in the matrix $\alpha$ shown in FIG. 6). Note, that since the T matrix is now an N×2 matrix, that matrix $\alpha$ needs to be a 2×M matrix, where the first row is populated with the $\alpha_0$ coefficients (i.e., $\alpha_{0\ 1,1}, \alpha_{0\ 1,2}, \ldots \alpha_{0\ 1,M}$), and the second row is populated with the $\alpha_1$ coefficients (i.e., $\alpha_{1\ 1,1}, \alpha_{1\ 1,2}, \ldots \alpha_{1\ 1,M}$). The $\alpha_0$ coefficients that were calculated in the first iteration using only Model Zero are discarded, so that new $\alpha_0$ coefficients are solved for, along with $\alpha_1$ coefficients. These coefficients will provide a best fit for the use of Model Zero and the first tent pole in predicting the Y-profiles. After solving for the coefficients in matrix $\alpha$, the prediction errors (residuals) are again calculated, using equation (3), where $\underline{\alpha}$ is a 2×M matrix in this iteration, and $\underline{T}$ is an N×2 matrix. Each row of $\underline{\alpha}$ may be considered a transform of the rows of Y. For linear regression, this transformation is linear.

Again, GSMILES determines the row of the $\epsilon$ matrix which has the maximum absolute value of error, in a manner as described above. Whatever technique is used to determine the maximum absolute error, the row from which the maximum absolute error is noted and used to identify the row (X-profile) from matrix 240, from which similarity values are again calculated. The calculated similarity values are used to populate the next column of values in the T matrix (in this iteration, the third column), which identifies the next tent pole in the model. The X-profile row selected for calculating the similarity values marks the location of the next (second, in this iteration) critical profile or "tent pole" identified by GSMILES for the model. A least squares regression algorithm is again performed, to perform the next iteration of the process, as described above. The GSMILES method can iterate through the above-described steps until the residuals come within the limits of the error range desired for the particular problem that is being solved, i.e., when the maximum error from matrix $\epsilon$ in any iteration falls below the error range. An example of an error threshold could be 0.01 or 0.1, or whatever other error level is reasonable for the problem being addressed. With each iteration, an additional tent pole is added to the model, thereby reducing the prediction error resulting in the overall model.

Alternatively, GSMILES may continue iterations as long as no two identified tent poles have locations that are too close to one another so as to be statistically indistinct from one another, i.e., significantly collinear. Put another way, GSMILES will not use two tent poles which are highly correlated and hence produce highly correlated similarity columns, i.e., which are collinear or nearly collinear (e.g., correlation squared ($R^2$)>95%, of the two similarity columns produced by the two X-profiles (tent pole locations). However, even if an X-profile is dissimilar (not near) all selected profiles in the model, it may still suffer collinearity problems with columns in the T-matrix as is. Hence, a tent-pole location is added to the model only if it passes both collinearity filters.

When a tent pole (row from matrix 240) is identified from the maximum absolute error in an $\epsilon$ matrix that is determined to be too close (nearly collinear) to a previously selected tent pole, GSMILES rejects this choice and moves to the next largest maximum absolute error value in that E matrix. The row in matrix 240 which corresponds to the next largest maximum absolute error is then examined with regard to the previously selected tent poles, by referring to the similarity column created for each respective selected X-profile. If this new row describes a tent pole which is not collinear or nearly collinear with a previously selected tent pole, then the calculated similarity values are inserted into a new column in matrix T and GSMILES processes another iteration. On the other hand, if it is determined that this row is nearly collinear or collinear with a previously chosen tent pole, GSMILES goes back to the $\epsilon$ matrix to select the next highest absolute error value. GSMILES iterates through the error selection process until a tent pole is found which is not collinear or nearly collinear with a previously selected tent pole, or until GSMILES has exhausted all rows of the error matrix $\epsilon$. When all rows of an error matrix $\epsilon$ have been exhausted, the model has its full set of tent poles and no more iterations of the above steps are processed for this model.

The last calculated $\alpha$ matrix ($\alpha$ profile from the last iteration performed by GSMILES) contains the values that are used in the model for predicting the Y-profile with an X-profile input. Thus, once GSMILES determines the critical support profiles and the $\alpha$ values associated with them, the model can be used to predict the Y-profile for a new X-profile.

Referring now to FIG. 8, an example is shown wherein a new X-profile (referred to as X*) is inputted to GSMILES in order to predict a Y-Profile for the same. For simplicity of explanation, this example uses only two tent poles, together with Model Zero, to characterize the GSMILES model. In practice, there will generally be many more tent poles employed. As a result, the $\alpha$ matrix in this example is a 3×M matrix, as shown in FIG. 8, and we have assumed, for example's sake, that the second profile is defined by the third row X-profile of the X-profile matrix 240. Therefore, the similarity values in column 3 of matrix T are populated by similarity values between row three of the X-profile matrix 240 and all rows in the S-profile matrix 240.

Again for simplicity, the example uses only a single X* profile, so that only a single row is added to the X-profile 240, making it an (N+1)×n matrix, with the N+1$^{st}$ row being populated with the X* profile values, although GSMILES is capable of handling multiple rows of X-profiles simultaneously, as would be readily apparent to those of ordinary skill in the art in view of the description of FIGS. 3–7 above.

Because the X-profile matrix has been expanded to N+1 rows, Model Zero in this case will also contain N+1 components (i.e., is an (N+1)×1 vector)) as shown in FIG. 8. The tent pole similarity values for tent poles one and two (i.e., columns 2 and 3) of the T matrix are populated with the previously calculated similarity values for rows 1–N. Row N+1 of the second column is populated with a similarity value found by calculating the similarity between row 7 and row N+1 (i.e., the X* profile) of the new X-profile matrix 240. Similarly, Row N+1 of the third column is populated with a similarity value found by calculating the similarity between row 7 and row N+1 (i.e., the X* profile) of the new X-profile matrix 240.

GSMILES then utilizes the $\alpha$ matrix to solve for the $Y_{N+1}$ profile using the $X_{N+1}$ profile (i.e., X* profile) using the following equation:

$$\underline{T} \cdot \underline{\alpha} = \underline{Y} + \underline{\epsilon} \quad (4)$$

where, for this example, $\underline{T}$=the N+1$^{st}$ row of the T matrix shown in FIG. 8,
$\underline{\alpha}$=the $\alpha$ matrix shown in FIG. 8,
$\underline{Y}$=the N+1$^{st}$ row of the matrix 340 shown in FIG. 8,
$\underline{\epsilon}$=a vector of M error values associated with the Y-profile outcome.

The error values will be within the acceptable range of permitted error designed into the GSMILES predictor according to the iterations performed in determining the tent poles as described above.

Typically, GSMILES overfits the data, i.e., noise are fit as systematic effects when in truth they tend to be random effects. The GSMILES model is trimmed back to the minimum of the sum of squared prospective ensemble errors to optimize prospective predictions, i.e., to remove tent poles that contribute to over fitting of the model to the data used to create the model, where even the noise associated with this data will tend to be modeled with too many tent poles.

Once the model is determined, the Z-columns of distribution-based U's are treated as linear score functions where the associated distribution, such as the binomial logistic model, for example, assigns probability to each of the score values.

The initial such Y-score function is estimated by properties of the associated distribution, e.g., for a two-category logistic, assign the value +1 for one class and the value −1 for the other class. Another method uses a high-order polynomial in a conventional distribution analysis to provide the score vector. The high order polynomial is useless for making any type of predictions however. The GSMILES model according to the present invention predicts this score vector, thereby producing a model with high quality and effective prediction properties. The GSMILES model can be further optimized by using the critical S-columns of the similarity matrix directly in the distributional optimization that could also include conventional X-variables and/or Model Zero. Hence, GSMILES provides a manageable set of high-leverage terms for distributional optimizations such as provided by generalized linear, mixed, logistic, ordinal, and survival model regression applications. In this fashion, GSMILES is not restricted to univariate binomial logistic distributions, because GSMILES can predict multiple columns of Y (in the Y-profile 340). Thus, GSMILES can simultaneously perform logistic regression, ordinal regression, survival regression, and other regression procedures involving multiple variable outcomes (multiple responses) as mediated by the score-function device. Some score functions produced by GSMILES do not require distributional models, but are useable as is. For example, for continuous variables, such as temperature, these outcomes can be analyzed by directly using the score function, without the need for logistic analysis. Other non-continuous variable outcomes may also not need logistic analysis, but may be used directly from a score function. For logistic regression, GSMILES assumes a binomial distribution pattern for scoring, while a multinomial distribution is assumed for ordinal regression and a Gaussian distribution is assumed for many other types of regression (continuous variables).

GSMILES can also fit disparate properties at the same time and provide score functions for them. For example, the Y columns may include distributional, text and continuous variables, all within the same matrix, which can be predicted by the model according to the present invention.

GSMILES can also perform predictions and similarity calculations on textual values. When text variables are included in the X-profile and/or the Y-profile, similarity calculations are performed among the rows of text, so that similarity values are also placed into the Y-profile, where the regression is performed with both predictor similarity values and predictee similarity values (i.e., similarity values are inserted on both sides of the equation, both in the X-profile, as well as the Y-profile).

The GSMILES methodology can also be performed on a basis of dissimilarity, by forming a dissimilarity matrix according to the same techniques described above. Since dissimilarity, or distance has an inverse relationship to similarity, one of ordinary skill in the art would readily be able to apply the techniques disclosed herein to form a GSMILES model based upon dissimilarity between the rows of the X-profile.

Leave-One-Out Cross-Validation

When modeling according to the GSMILES methodology, as with any type of prediction model, both fit error (training error) and validation error (test error) are encountered. In this case, fit error is the error that results in the $\epsilon$ matrix at the final iteration of determining the $\alpha$ matrix according to the above-described methodology, as GSMILES optimizes the training set (N×n matrix 240) to predict the training set Y-profile 340 (N×M matrix). Validation error is the error resulting from applying the model to an independent data set. For example, the validation error resulting in the example described above with regard to FIG. 8 is the $\epsilon$ vector containing the M values of error associated with the N+1$^{st}$ row of the matrix 340 shown in FIG. 8.

In general, to determine test or validation error, the model determined with the training set is applied to an independent set of data (the test or validation set) which has known Y-outcome values. The model is applied to the X-profile of the test set to determine the Y-profile. The calculated Y-profile is then compared with the known Y-profile to calculate the test or validation error, and the test or validation error is then examined to determine whether it is within the preset, acceptable range of error permitted by the model. If the test or validation error is within the predefined limits of the error range, than the model passes the validation test. Otherwise, it may be determined that the model needs further revision, or other factors prevent the model from being used with the test profile. For example, the test profile may contain some X values that are outside the range of X-values that the present model can effectively form predictions on. Some of the X-variables may have little association with the Y-profiles and hence they contribute non-productive variations thereby reducing the efficiency of the GSMILES modeling process. Hence, more data would be required to randomize out the useless variations of such non-productive X-variables. Optionally, one can identify and eliminate such noisy X-variables, since they tend to have very low rank via the Marquardt-Levenberg (ML) ranking method described in this document. To identify a rank threshold between legitimate and noisy X-variables, an intentional noisy variable may be included in the X-profile and its ML rank noted. Repetition of this procedure with alternate versions of the noisy X-column, e.g., by random number generations, produces a distribution of such noise ranks, whose statistical properties may be used to set an X-noise threshold.

The leave-one-out cross-validation technique involves estimating the validation error through use of the training set. As an example, assuming that matrix 240,340 in FIG. 3 is the initial training set, the leave-one-out technique involves extracting one of the rows of the training set prior to carrying out the GSMILES methodology to solve for similarity and the $\alpha$ matrix that are described above. So, in this case, the "altered" training set will include an X-profile which is an (N−1)×n matrix and a Y-profile which is an (N−1)×M matrix. The extracted row (for a non-limiting example, we can assume that row 5 was extracted) becomes the validation set that will be used after solving for the GSMILES model.

Using the altered training data set, an $\alpha$ matrix is solved for using the techniques described above with regard to the GSMILES least squares methodology. After determining the $\alpha$ matrix, this $\alpha$ matrix is then used to predict the outcome for the extracted row (i.e., the test set, row 5 in the current example). Because the Y-profile of the test set is known, the known Y-values can be compared with the predicted Y-values to determine the validation error and to determine whether this validation error is within the acceptable range of error.

The same procedure may be carried out for each row of the original training data set 240,340, one row at a time. In this way, each profile used in the training data set can be used independently as a validation data set. By summing the squares of the errors derived from each extracted row and dividing by the number or rows, a variance can be determined for the validation error (i.e., validation variance). However, to require validation error to be determined by completely processing through the GSMILES methodology to independently determine an $\alpha$ matrix for each extracted row, is to require a great deal of processing time, particularly for typical data sets which may contain thousands of rows. This is both time consuming and expensive, and therefore inefficient.

For simplicity and clarity, standard notation is used in the following discussion wherein a single variable denoted y is a function of a vector of variables denoted by x. Note that this x actually represents the T-rows in the GSMILES formulism referred to above. Without loss of generality consider a single y-variable as a function of multiple x-variables. A generalized solution for the Leave-One-Out (LOO) cross-validation statistic for a model f(x; $\alpha$) trained on a data set D={(x$_1$, y$_1$), . . . ,x$_n$,y$_n$)}, x$_i \in$R$^m$, y$_i \in$R, where a single data point (x$_i$, y$_i$) is removed, results in a training set D$_i$ and a predictor f$_i$(x, $\alpha$). The difference between the observation y$_i$ and what a model predicts in the absence of (x$_i$, y$_i$) is $\epsilon_i$=y$_i$−f$_i$(x$_i$, $\alpha$). The Leave-One-Out (LOO) cross-validation statistic predicts the variance in this error:

$$\sigma_{LOO}^2 = \frac{1}{n}\sum_{i=1}^{n} \varepsilon_i^2 \qquad (5)$$

Rather than evaluating LOO by retraining the model n times, a formulation which relates $\sigma_{LOO}^2$ to the quantities already used in training f(x; $\alpha$) is needed in order to avoid the inefficiencies and expense of completely processing through the GSMILES methodology to independently determine an $\alpha$ vector for each extracted row, as alluded to above. This is possible for linear models f(x; $\alpha$)=$\alpha^T$x, $\alpha \in$R$^m$. If the data matrix and response vector are defined as:

$$X = \begin{pmatrix} x_1^T \\ x_2^T \\ \vdots \\ x_n^T \end{pmatrix} \qquad y = \begin{pmatrix} y_1 \\ y_2 \\ \vdots \\ y_n \end{pmatrix} \qquad (6)$$

then the linear least squares solution $\alpha$ and corresponding residual $\rho$ are:

$$\alpha = (X^T X)^{-1} X^T y \qquad (7)$$

$$\rho = y - X\alpha \quad (8)$$

$$= y - X(X^TX)^{-1}X^Ty \quad (9)$$

$$= (I - X(X^TX)^{-1}X^T)y \quad (10)$$

$$= Py \quad (11)$$

where $P \equiv I - X(X^TX)^{-1}X^T$ is the n×n projection matrix. If the first data point is partitioned from the data matrix, the abbreviated training set defines a matrix $\overline{X}$ and response vector $\overline{y}$ related to the original as follows:

$$X = \begin{pmatrix} x_1^T \\ \overline{X} \end{pmatrix} \qquad y = \begin{pmatrix} y_1 \\ \overline{y} \end{pmatrix} \quad (12)$$

$$X^TX = \overline{X}^T\overline{X} + x_1^Tx_1 \quad (13)$$

$$X^Ty = \overline{X}^T\overline{y} + y_1x_1 \quad (14)$$

The least squares solution of the truncated data set is:

$$\overline{\alpha} = (\overline{X}^T\overline{X})^{-1}\overline{X}^T\overline{y} \quad (15)$$

The prediction error resulting from the removal of the first row is therefore:

$$\epsilon_1 = y_1 - \overline{\alpha}^T x_1 \quad (16)$$

The relationships defined in equations (12), (13) and (14) are next used to replace $\overline{X}$, $\overline{y}$ and $\overline{\alpha}$. First, the Sherman-Morrison-Woodbury formula establishes that:

$$(\overline{X}^T\overline{X})^{-1} = \quad (17)$$

$$(X^TX - x_1^Tx_1)^{-1} = (X^TX)^{-1} + \frac{(X^TX)^{-1}x_1x_1^T(X^TX)^{-1}}{1 - x_1^T(X^TX)^{-1}x_1}$$

For the sake of abbreviation, define $F = (X^TX)^{-1}$, $d_1 = x_1^T F x_1$, and $u_1 = 1 - d_1$. Note that $u_1$ and $d_1$ are scalars. Substituting these relationships gives:

$$= \left[F + \frac{1}{u_1}Fx_1x_1^TF\right](X^Ty - y_1x_1) \quad (18)$$

$$= \frac{1}{u_1}[u_1 F + Fx_1x_1^TF](X^Ty - y_1x_1) \quad (19)$$

$$= \frac{1}{u_1}[u_1 F(X^Ty - y_1x_1) + Fx_1x_1^TF(X^Ty - y_1x_1)] \quad (20)$$

$$= \frac{1}{u_1}[u_1 FX^Ty - u_1 y_1 Fx_1 + Fx_1x_1^T FX^Ty - y_1 d_1 Fx_1] \quad (21)$$

Returning to the prediction error of equation (16) and substituting with the above developed relationship gives:

$$\epsilon_1 = y_1 - \overline{\alpha}^T x_1 \quad (16)$$

$$= y_1 - x_1^T \overline{\alpha} \quad (22)$$

$$= \frac{1}{u_1}(u_1 y_1 - x_1^T(u_1 \overline{\alpha})) \quad (23)$$

$$= \frac{1}{u_1}[u_1 y_1 - u_1 x_1^T FX^Ty + \quad (24)$$
$$u_1 y_1 x_1^T Fx_1 - x_1^T Fx_1 x_1^T FX^T y + y d_1 x_1^T Fx_1]$$

$$= \frac{1}{u_1}[u_1 y_1 - u_1 x_1^T FX^Ty + u_1 y_1 d_1 - d_1 x_1^T FX^Ty + y_1 d_1^2] \quad (25)$$

$$= \frac{1}{u_1}[u_1 y_1 (1 + d_1) - (u_1 + d_1) x_1^T FX^Ty + y_1 d_1^2] \quad (26)$$

$$= \frac{1}{u_1}[(1 - d_1)y_1(1 + d_1) + y_1 d_1^2 - x_1^T FX^Ty] \quad (27)$$

$$= \frac{1}{u_1}[y_1(1 - d_1^2) + y_1 d_1^2 - x_1^T FX^Ty] \quad (28)$$

$$= \frac{1}{u_1}[y_1 - x_1^T FX^Ty] \quad (29)$$

$$= \frac{y_1 - x_1^T(X^TX)^{-1}X^Ty}{1 - x_1^T(X^TX)^{-1}x_1} \quad (30)$$

By noting that $y_1 = e_1^T y$ and $x_1^T = e_1^T X$, where $e_1 = [1\ 0\ 0\ \ldots\ 0]^T$, gives:

$$\epsilon_1 = \frac{e_1^T y - e_1^T X(X^TX)^{-1}X^T y}{1 - e_1^T X(X^TX)^{-1}X^T e_1} \quad (31)$$

$$= \frac{e_1^T(I - X(X^TX)^{-1}X^T)y}{e_1^T(I - X(X^TX)^{-1}X^T)e_1} \quad (32)$$

$$= \frac{e_1^T P y}{e_1^T P e_1} \quad (33)$$

$$= \frac{e_1^T \rho}{e_1^T P e_1} \quad (34)$$

$$= \frac{\rho_1}{e_1^T P e_1} \quad (35)$$

$$= \frac{\rho_1}{P_{11}} \quad (36)$$

From this it can be observed that the prediction error resulting from the removal of the first data point is the ratio of the first element of the residual and the first diagonal element of the projection matrix. Since any data point $(x_i, y_i)$ can be permuted to the first row without changing the solution, the conclusion is reached, without any loss of generality, that:

$$\epsilon_t = \frac{\rho_t}{P_{ii}} \quad (37)$$

and $$\sigma_{LOO}^2 = \frac{1}{n}\sum_{i=1}^{n}\left(\frac{\rho_i}{P_{ii}}\right)^2 \quad (38)$$

In order to compute $\sigma_{LOO}^2$ in the context of sequential least-squares processing such as used in the GSMILES methodology (because later it is a useful metric for trimming to the optimal subset of basis vectors (i.e., tent poles)), in each iteration k+1 of the algorithm, a column $a_{k+1}$ is added to the data matrix $X_k$ (e.g., such as data matrix 240). This gives the general formula:

$$X_{k+1} = [X_k a_{k+1}] \tag{39}$$

When n is large, forming the projection matrix P in order to extract its diagonal elements is impractical, requiring n×n memory, which could exceed the limits of current hardware. It is also computationally expensive, making it infeasible to recompute at every iteration k. Instead, the QR factorization of $X_k$ is computed at every iteration, where:

$$X_k = Q_k R_k = Q_k \begin{pmatrix} \overline{R}_k \\ 0 \end{pmatrix} \tag{40}$$

Where $X_k \in R^{n \times k}$, $Q_k \in R^{n \times n}$, $R_k \in R^{n \times k}$, $\overline{R}_k \in R^{k \times k}$. $\overline{R}_k$ is upper triangular and $Q_k$ is orthogonal. By design, it is also non-singular. $Q_k^T$ is a product of Householder matrices, as follows:

$$Q_k^T = H_k H_{k-1} \ldots H_1 \tag{41}$$

Each Householder matrix is dependent only on $v_k \in R^n$, the Householder vector:

$$H_k = I - T_k v_k v_k^T \tag{42}$$

Where $T_k = 2 / v_k^T v_k$. An efficient implementation of the algorithm will not store $Q_k$ or any of its factors explicitly. Only the product of $Q_k$ with some n vector g, $Q_k^T g$, or $Q_{kg}$ is needed. For this purpose, storing the set of Householder vectors $\{v_1, v_2, \ldots v_k\}$ is sufficient. By design, $v_k$ has the following special structure: $v_k^T = [0 \ldots 0 \; 1 \; B \ldots B]$, where the 0 elements extend over k−1 columns and the B elements extend over n−k columns. A recursive relationship for the projection matrix P can now be shown at the $k^{th}$ iteration, $P_k$:

$$P_k = I_n - X_k (X_k^T X_k)^{-1} X_k^T \tag{43}$$

$$= I_n - (Q_k R_k)(R_k^T Q_k^T Q_k R_k)^{-1} (R_k^T Q_k^T) \tag{44}$$

$$= I_n - Q_k R_k (R_k^T R_k)^{-1} (R_k^T Q_k^T) \tag{45}$$

$$= I_n - Q_k \begin{pmatrix} R_k \\ 0 \end{pmatrix} \left( [\overline{R}_k^T \; 0] \begin{pmatrix} R_k \\ 0 \end{pmatrix} \right)^{-1} [\overline{R}_k^T \; 0] Q_k^T \tag{46}$$

$$= I_n - Q_k \begin{pmatrix} R_k \\ 0 \end{pmatrix} (\overline{R}_k^T \overline{R}_k)^{-1} [\overline{R}_k^T \; 0] Q_k^T \tag{47}$$

$$= I_n - Q_k \begin{pmatrix} \overline{R}_k (\overline{R}_k^T \overline{R}_k)^{-1} \overline{R}_k^T & 0 \\ 0 & 0 \end{pmatrix} Q_k^T \tag{48}$$

$$= I_n - Q_k \begin{pmatrix} \overline{R}_k (\overline{R}_k)^{-1} (\overline{R}_k^T)^{-1} \overline{R}_k^T & 0 \\ 0 & 0 \end{pmatrix} Q_k^T \tag{49}$$

$$= I_n - Q_k \begin{pmatrix} I_k & 0 \\ 0 & 0 \end{pmatrix} Q_k^T \tag{50}$$

$$= I_n - H_1 \ldots H_{k-1} H_k \begin{pmatrix} I_k & 0 \\ 0 & 0 \end{pmatrix} H_k H_{k-1} \ldots H_1 \tag{51}$$

Furthermore, $$H_k \begin{pmatrix} I_k & 0 \\ 0 & 0 \end{pmatrix} H_k = (I_n - T_k v_k v_k^T) \begin{pmatrix} I_k & 0 \\ 0 & 0 \end{pmatrix} (I_n - T_k v_k v_k^T) = \tag{52}$$

$$\begin{pmatrix} I_k & 0 \\ 0 & 0 \end{pmatrix} - T_k v_k v_k^T \begin{pmatrix} I_k & 0 \\ 0 & 0 \end{pmatrix} - T_k \begin{pmatrix} I_k & 0 \\ 0 & 0 \end{pmatrix} v_k v_k^T$$

$$+ T_k^2 v_k v_k^T \begin{pmatrix} I_k & 0 \\ 0 & 0 \end{pmatrix} v_k v_k^T \tag{53}$$

As a result of the special structure of $v_k$, $$\begin{pmatrix} I_k & 0 \\ 0 & 0 \end{pmatrix} v_k = e_k, \text{ and} \tag{54}$$

$$e_k^T v_k = 1 \tag{55}$$

and thus, $$H_k \begin{pmatrix} I_k & 0 \\ 0 & 0 \end{pmatrix} H_k = \begin{pmatrix} I_k & 0 \\ 0 & 0 \end{pmatrix} - T_k v_k e_k^T - T_k e_k v_k^T + T_k^2 v_k e_k^T v_k v_k^T \tag{56}$$

$$= \begin{pmatrix} I_k & 0 \\ 0 & 0 \end{pmatrix} - T_k v_k e_k^T - T_k e_k v_k^T + T_k^2 v_k v_k^T \tag{57}$$

$$= \begin{pmatrix} I_{k-1} & 0 \\ 0 & 0 \end{pmatrix} + e_k e_k^T - T_k v_k e_k^T - T_k e_k v_k^T + T_k^2 v_k v_k^T \tag{58}$$

$$= \begin{pmatrix} I_{k-1} & 0 \\ 0 & 0 \end{pmatrix} + (e_k - T_k v_k)(e_k - T_k v_k)^T \tag{59}$$

$$= \begin{pmatrix} I_{k-1} & 0 \\ 0 & 0 \end{pmatrix} + z_k z_k^T \tag{60}$$

where $z_k \equiv e_k - T_k v_k$. Returning to $P_k$, we now have:

$$P_k = I_n - H_1 \ldots H_{k-1} \left( \begin{pmatrix} I_{k-1} & 0 \\ 0 & 0 \end{pmatrix} + z_k z_k^T \right) H_{k-1} \ldots H_1 \tag{61}$$

$$= I_n - \tag{62}$$

$$H_1 \ldots H_{k-1} \left( \begin{pmatrix} I_{k-1} & 0 \\ 0 & 0 \end{pmatrix} H_{k-1} \ldots H_1 - H_1 \ldots H_{k-1} z_k z_k^T H_{k-1} \ldots H_1 \right)$$

$$= P_{k-1} - Q_{k-1} z_k z_k^T Q_{k-1}^T \tag{63}$$

$$= P_{k-1} - w_k w_k^T \tag{64}$$

where $w_k \equiv Q_{k-1} z_k$. Finally, the $i^{th}$ diagonal element of the projection matrix is $$(P_k)_{ii} = e_i^T (P_{k-1} - w_k w_k^T) e_i \tag{65}$$

$$= (P_{k-1})_{ii} - e_i^T w_k w_k^T e_i \tag{66}$$

$$= (P_{k-1})_{ii} - (w_k)_i^2 \tag{67}$$

where $$T_k = \frac{2}{v_k^T v_k} \tag{68}$$

$$z_k = e_k - T_k v_k \tag{69}$$

$$w_k = Q_{k-1} z_k \tag{70}$$

and $$P_0 = I_n \tag{71}$$

Hence, one has an LOO sum of squared residuals for every y-column in matrix Y. Optionally, using an ensemble error for each row produces an ensemble LOO sum of squared residuals as is used by GSMILES.

Figure 9:
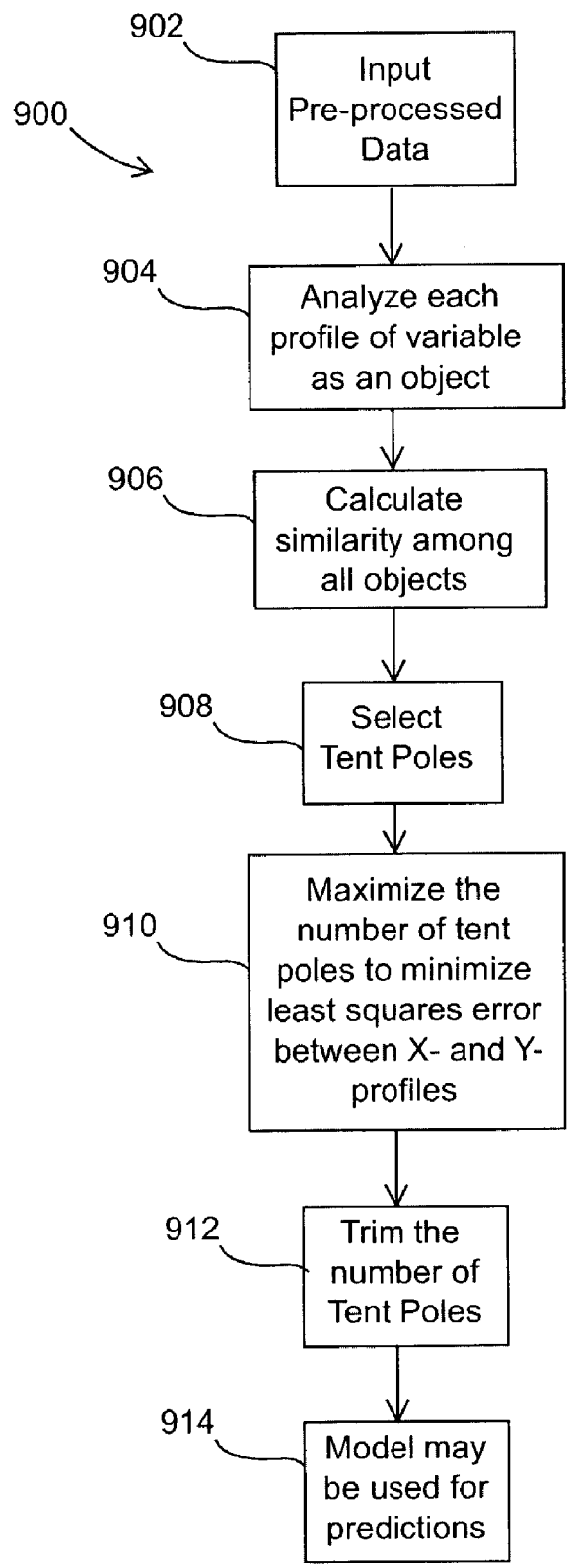
FIG. 9 is a flow chart showing one example of an iterative procedure employed by GSMILES in determining a predictor model.

Referring now to FIG. 9, a flow chart 900 identifies some of the important process steps in one example of an iterative procedure employed by GSMILES in determining a predictor model. At step 902, GSMILES module 140 receives inputted data which has been preprocessed according to one or more of the techniques described above. Each profile of associated measurements of variables of the inputted data is treated as an object by GSMILES at step 904, with potentially three classes of information: predictor/driver variables (X-variables), predictee/consequential variables (Y-variables), and nuisance variables (noise variables, known and unknown). Note that these classes are not mutually exclusive; hence, a variable can belong to one or more of these GSMILES classes as dictated by the particular analysis being processed.

GSMILES calculates similarity among all objects at step 906, according to the techniques described above. Note that similarity may be compound, e.g., a combination of similarity measures, where each similarity component is specific to a subset of X-profile variables. Note further, that GSMILES may just as well calculate dissimilarity among all objects to arrive at the same results, but for sake of simplicity, only the similarity calculation method is described here, as an example. It would be readily apparent to those of ordinary skill in the statistic arts, as to how to proceed on a basis using dissimilarity. GSMILES uses the similarity values to predict the Y-variables, as described above. However, GSMILES is not limited to predicting Y-variables, but may also be used to predict the X-variables themselves, via the similarity matrix, an operation that functions as a noise filter, or smoothing function, to arrive at a more stable set of X variables. GSMILES may also be used to solve for X-variables and Y-variables simultaneously. When text variables are involved, these variables may appear in one or both of X- and Y-profiles. GSMILES calculates similarity among the text variables, and provides similarity values for these text values with regard to the X-profile, as well as the Y-profile when text is present in the Y-profile. Hence, the set of text Y-variables are replaced by a similarity column to form the new Y-matrix, Y2-matrix.

Using the similarity values, GSMILES selects a critical subset of objects (identifying the locations of the tent poles) at step 908, that can optimally predict the Y-values (or other values being solved for) of all objects within the precision limitations imposed by nuisance effects, assured by statistically valid criteria. The selection may be made by an iterative algorithm as was discussed above, and which is further referred to below.

Upon identification of the tent pole locations and similarity values representing the tent poles, as well as an estimation of the X-nonlinear transformation ("α values") of the Y-profiles associated with the strategic X-profiles (tent poles) by least squares regression or other optimization technique, GSMILES maximizes the number of tent poles at step 910 to minimize the sum of squared prospective errors between the X- and Y-profiles. At step 912, GSMILES then trims back the number of tent poles (by "trimming", as described above), where the GSMILES model is trimmed back to the minimum of the prospective sum of squares to optimize prospective predictions, i.e., to remove tent poles that contribute to over fitting of the model to the data used to create the model, where even the noise associated with this data will tend to be modeled with too many tent poles.

Trimming may be carried out with the aid of Leave-One-Out cross validation techniques, as described above, or by other techniques designed to compare training error (fit error) with validation error (test error) to optimize the model.

Figure 11:
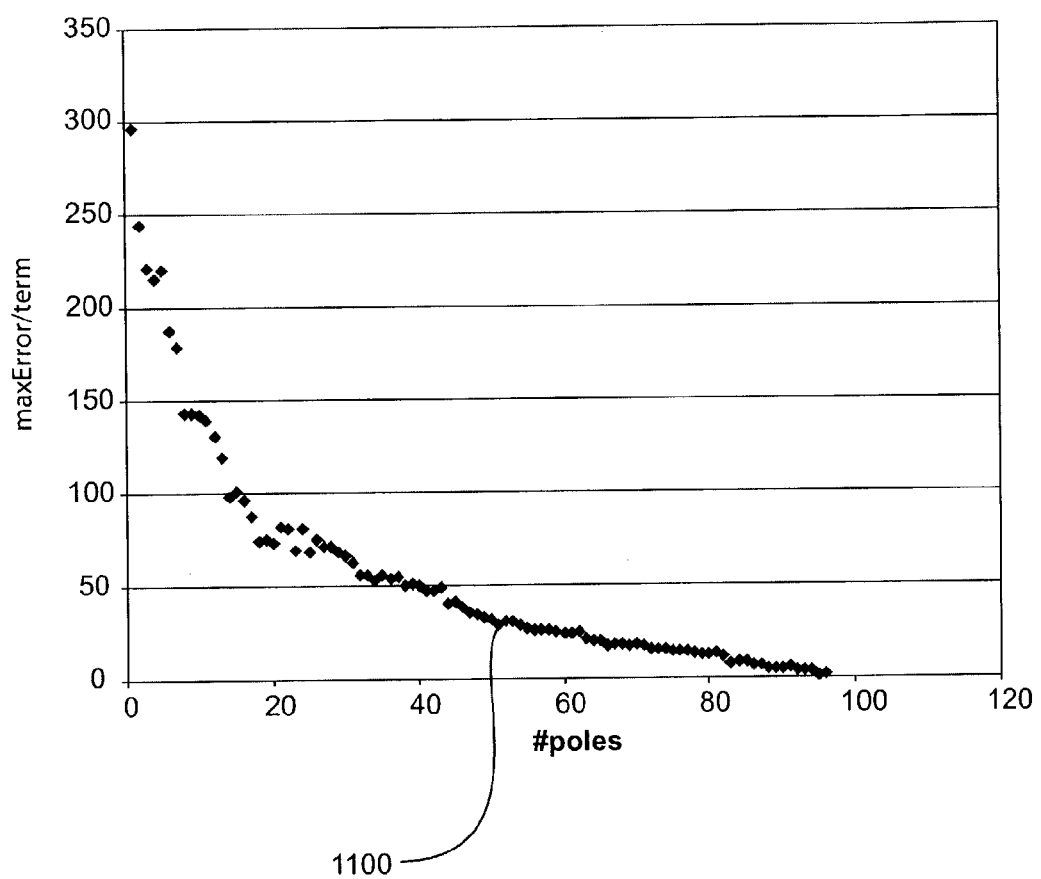
FIG. 11 is a graph plotting the maximum absolute (ensemble) error versus the number of tent poles used in developing a model (training or fit error versus the number of tent poles).
Figure 12:
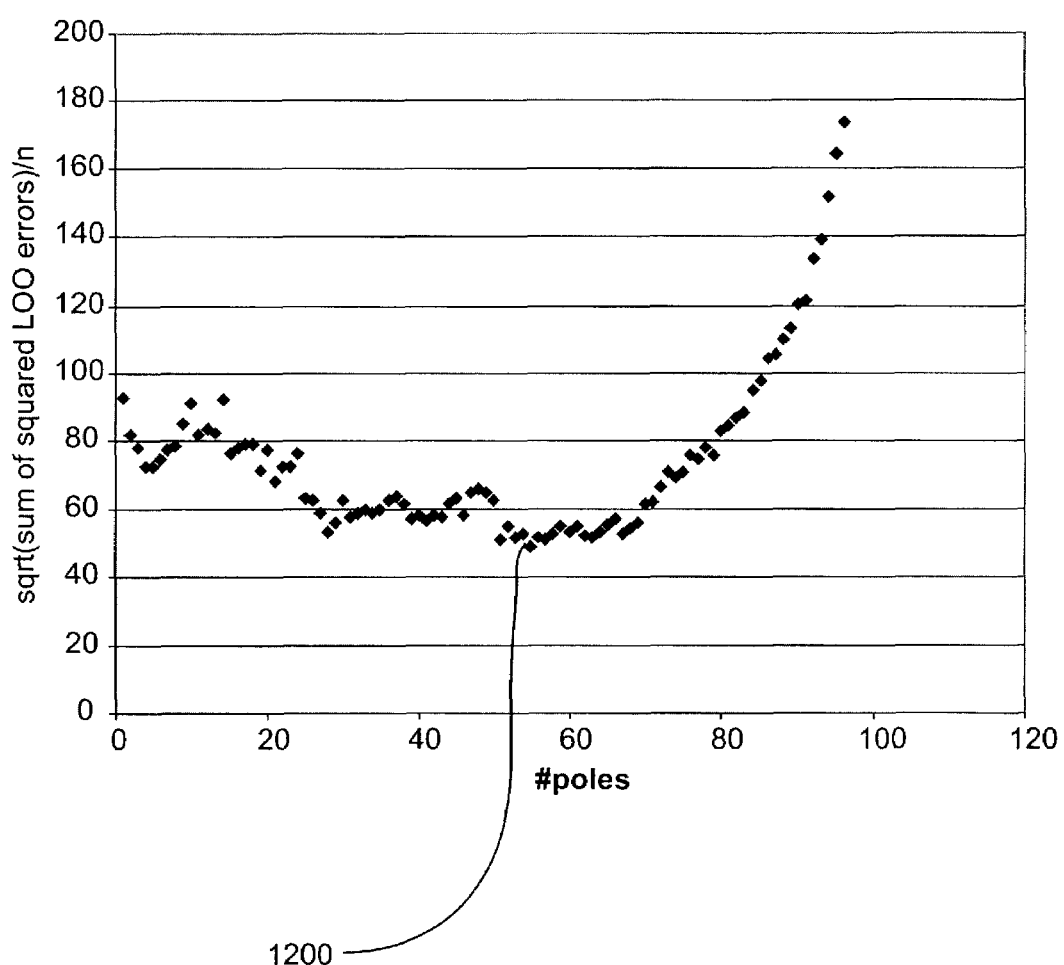
FIG. 12 is a graph plotting the square root of the sum of the squared LOO errors divided by the number of terms squared against the number of tent poles, as a measure of test or validation error

FIGS. 11 and 12 illustrate an example of such comparison. FIG. 11 plots 1100 the maximum absolute (ensemble) error versus the number of tent poles used in developing the model (training or fit error versus the number of tent poles). It can be observed in FIG. 11, that the error asymptotically approaches a perfect fit as the number of poles is increased. FIG. 12 graphs 1200 the square root of the sum of the squared LOO errors divided by the number of terms squared and plot this against the number of tent poles, as a measure of test or validation error (described above). It can be seen from FIG. 12, that somewhere in the range of 60–70 tent poles, the error terms stop decreasing and begin to rapidly increase. By comparing the two charts of FIGS. 11 and 12, GSMILES makes the determination to trim the number of poles to the number that correlates to the location of the chart of FIG. 12 where the error starts to diverge (somewhere in the range of 60–70 in FIG. 12, although GSMILES would be able to accurately identify the number where the minimum occurs, which is the point where divergence begins). The poles beyond this number are those that contribute to fitting the noise or nuisance variables in the chart of FIG. 11.

After optimization of the model, the model is ready to be used in calculating predictions at step 914. Upon calculating prediction values, the present invention may optionally employ a scoring method. Score functions are optimized for every outcome in the modeling process. For example, multivariate probabilities of survival and/or categorical outcomes can be optimally assigned to the GSMILES scores. If appropriate, the distributional property of each outcome is then used to optimally assign a probability function to its score function. The modeled score/probability functions may be used to find regions of profiles that satisfy all criteria/specifications placed upon the multiple outcomes. The profile components can be ranked according to their importance to the derived multi-functionality.

Figure 10:
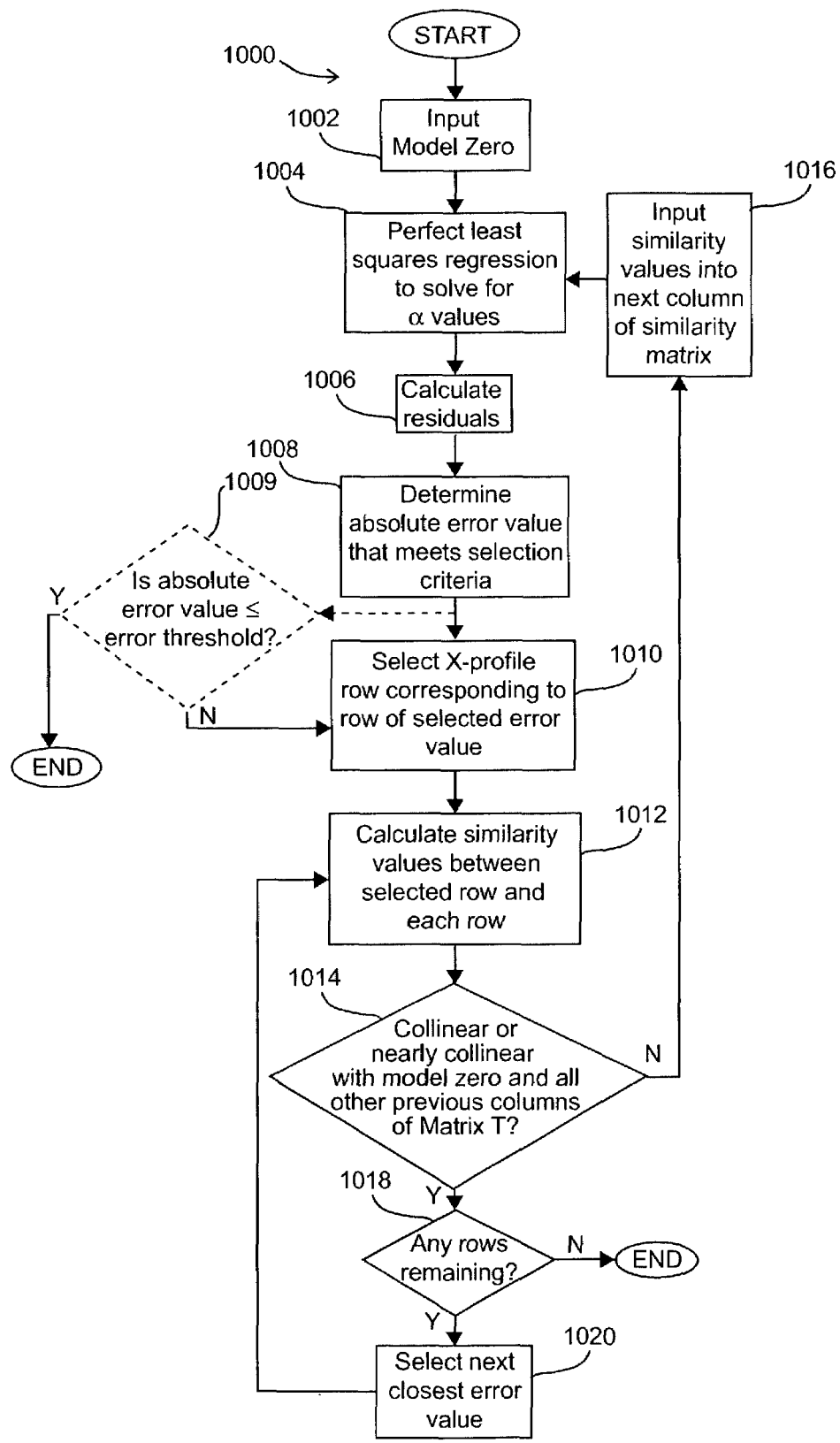
FIG. 10 is a flow chart representing some of the important process steps in one example of an iterative algorithm that the present invention employs to select the columns of a similarity matrix.

FIG. 10 is a flow chart 1000 representing some of the important process steps in one example of an iterative algorithm that GSMILES employs to select the columns of a similarity matrix, such as similarity matrix T described above. To solve for the critical profiles, an initial model (i.e., Model Zero) is inputted to the system at step 1002, in matrix T, as described above with regard to FIG. 5. A least squares regression is next performed at step 1004 to solve for the α coefficients (in this iteration, it is the $α_0$ coefficients) which provide a best fit for the use of the model (which includes only Model Zero in this iteration) to predict the Y-profiles (or X-profiles or X- and Y-profiles, or whatever the output variables have been defined as, as discussed above).

Next, the residuals (prediction errors e) are calculated at step 1006, as described in detail above with regard to FIGS. 5–6. The residual values are then analyzed by GSMILES to determine the absolute error value that meets a predefined selection criteria. As described above, one example of a predefined selection criterion is maximum absolute error, which may be simply selected from the residuals when the residual is a vector. However, when the residuals take the form of a matrix, as in FIG. 6, an ensemble error is calculated for each row of the matrix by GSMILES, where the ensemble error is defined to leverage communalities. The ensemble errors are then used in selecting according to the selection criteria. Examples of ensemble error calculations are described above. Although the above examples use maximum absolute error as the selection criterion, other criteria may be alternatively used. Examples of alternative criteria are mean (ensemble) absolute error, median (ensemble) absolute error, mode (ensemble) absolute error, weighted average (ensemble) absolute error, robust average (ensemble) absolute error, or other predefined error measure. The residual error value (or ensemble residual error value) meeting the selection criterion is identified at step 1008.

GSMILES then selects the X-profile row from the input matrix (e.g., matrix 240) that corresponds to the row of the residual matrix from which the residual error (or ensemble error) was selected. This identifies a potential location of a tent pole to be used in the model. At step 1012, GSMILES then calculates similarity (or dissimilarity) values between the selected X-profile row and each row of the input matrix (including the selected row) and uses these similarity values to populate the next column of the similarity matrix T, assuming that the selected X-profile row is not too close in its values (e.g., collinear or nearly collinear) with another X-profile row that has already been previously selected, as determined in step 1014.

If it is determined that the values are not collinear or nearly collinear with a previously selected tent pole profile, then the similarity values calculated in step 1012 are inputted to the next column of similarity matrix T at step 1016. The process then returns to step 1004 to perform another least squares regression using the new similarity matrix. If the column of the selected row selected is determined to be collinear or nearly collinear with Model Zero and all other columns of matrix T (from previously selected X-profile rows), via step 1014, GSMILES rejects the currently selected X-profile row and does not use it for a tent pole (of course, it wouldn't determine this in the first iteration if Model Zero were selected as a null set, since there would be no previously selected rows). Then GSMILES determines whether there are any remaining rows of the X-profile which have not already been selected and considered at step 1018. If all rows have not yet been considered, then GSMILES goes back to the residual error values, and selects the next error (or ensemble) error value that is next closest to the selection criterion at step 1020. For example, if the selection criterion is maximum absolute value, GSMILES would select the row of the residual values that has the second highest absolute error at this stage of the cycle.

Processing then returns to step 1012 to calculate similarity values for the newly selected row. This subroutine is repeated until a new tent pole is selected which is not collinear or nearly collinear with Model Zero and all previous T-columns, or until it is determined at step 1018 that all rows have been considered. When all rows have been considered, the similarity matrix has been completed, and no more tent poles are added.

An optional stopping method is shown in step 1009, where, after the step of determining the absolute error or ensemble error value that meets the selection criteria in step 1008, GSMILES determined whether the selected absolute error value is less than or equal to a predefined error threshold for the current model. If the selected error value is less than or equal to the predefined error threshold, then GSMILES determines that the similarity matrix has been completed, and no more tent poles are added. If the selected error value is greater than the predefined error threshold, then processing continues to step 1010. Note that step 1009 can be used in conjunction with steps 1014, 1018 and 1020, or as an alternative to these steps.

As alluded to above, the GSMILES predictor model can be used to fit a matrix to a matrix, e.g. to fit a matrix of X-profiles to itself, inherently using eigenvalue analysis and partial least squares processing. Thus, the X-profile values may be used to fit themselves through a one dimensional linear transformation, i.e., a bottleneck, based on the largest singular-value eigenvalue of that matrix. Using the techniques described above, the same procedure is used to develop a similarity matrix, only the X-profile matrix replaces the Y-profile matrix referred to above. This technique is useful for situations where some of the X values are missing in the X-profile (missing data), for example. In these situations, a row of X-profile data may contain known, useful values that the researcher doesn't necessarily want to throw out just because all values of that row are not present. In such an instance, imputation data may be employed, where GSMILES (or the user) puts in some estimates of what the missing values are. Then GSMILES can use the completed X-profile matrix to predict itself. This produces predictions for the missing values which are different from the estimates that were put in. The predictions are better, because they are more consistent with all the values in the matrix, because all of the other values in the matrix were used to determine what the missing value predictions are. Initial estimates of the missing values may be average X values, or some other starting values which are reasonable for the particular application being studied. When the predictions are outputted from GSMILES, they can then be plugged into the missing data locations, and the process may be repeated to get more refined predictions. Iterations may be performed until differences between the current replacement modifications and the previous iteration of replacement modifications are less than a pre-defined threshold value of correction difference.

Another use for this type of processing is to use it as an effective noise filter for the X-profile, wherein cycling the X-profile data through GSMILES as described above (whether there is missing data or not) effectively smoothes the X-profile function, reduce noise levels and acting as a filter. This results in a "cleaner" X-profile.

Still further, GSMILES may be used to predict both X- and Y-profiles simultaneously, using the X-profile also to produce tent poles. This again is related to eigenvalue analysis and partial least squares processing, and dimensional reduction or bottlenecking transformations. Note that GSMILES inherently produces a nonlinear analogy of partial least squares. However, partial least squares processing may possibly incorrectly match information (eigenvalues) of the X- and Y-matrices. To prevent this possibility, GSMILES may optionally use the X-profile matrix to simultaneously predict both X- and Y-values in the form of a combined matrix, either stacked vertically or concatenated horizontally. If the relative weight of each matrix within the combination is about equal, then one achieves correct matching of the eigenvalues. The nonlinear version of this method is accomplished by using the X-profile to predict both the X- and Y-profiles using GSMILES.

Still further, it is possible to simultaneously remove noise, impute missing X-values, and analyze causal relationships between the rows (profiles) of the concatenated version X/Y of the two matrices (X- and Y-profiles), by using GSMILES to model X/Y as both input and output. Optionally to enhance causal leverage, GSMILES is not allowed to use Y-profiles in the input X/Y for tent-pole selection. Hence, strategic profiles may be found in the X-profile part of the X/Y input matrix to optimally predict all profiles in X stacked on Y, symbolized by X/Y. GSMILES can then cluster the resulting profiles in the prediction-enhanced X/Y matrix. This is a form of synchronization that tends to put associated heterogeneous profiles such as phenotypic properties versus gene-expression properties, for example, into the same cluster. This method is useful to identify gene expression profiles and compound activity profiles that tend to synchronize or anti-synchronize together, suggesting some kind of interaction between the genes and compounds in each cluster.

The importance of each X-variable is determined by the Marquardt-Levenberg (ML) method applied to the GSMILES model. Hence, this process is leveraged by all Y-variables and their internal relationships, such as communalities induced by common phenomena, which common phenomena are often unknown. GSMILES may multiply a coefficient onto each variable to express the ellipticity of the basis set as a function of the X space. Typically, these coefficients are assumed to be constant with a value of unity, i.e., signifying global radial symmetry over the X space. The Marquardt-Levenberg algorithm can be used to test this assumption. A byproduct of use of the Marquardt-Levenberg algorithm in this manner is the model leverage associated with each coefficient and hence, each variable. This leverage may be used to rank the X-variables.

The GSMILES nodes (tent poles) are localized basis functions based on similarity between locations in the model domain (X-space). The spans of influence of each basis function are determined by each function's particular decay constants. The bigger a constant is, the faster the decay, and hence the smaller the influence region of the node surrounding its domain location. The best decay value depends both on the density of data adjacent to the node location, clustering properties of the data, and the functional complexity of the Y-ensemble there. For example, if the Y-ensemble is essentially constant in the domain region containing the node location, then all adjacent data are essentially replicates. Hence, the node function should essentially average these adjacent Y-values. However, beyond such adjacent data, the node influence should decay appropriately to maintain its localized status. If decay is too fast, then the basis function begins to act like a delta function or dummy spike variable and cannot represent the possible systematic regional trends. If decay is too slow, the basis function begins to act like a constant. The same concept applies to data clusters in place of individual data points. In that respect, note that individual data points may be considered as clusters of size or membership of one element.

To determine appropriate decay constants for each domain location in the data, GSMILES determines the working dimension of the domain at each data location, and then computes a domain simplex of data adjacent to each such location. The decay constant for each location is set to the inverse of the largest of the dissimilarity values between each location and the simplex of adjacent data. This normalizes the dissimilarity function for each node according to the data density at the node. In this case, the normalized dissimilarity becomes unity at the most dissimilar location within the simplex of adjacent data for each location in the domain (X-space) of the data. Optionally, GSMILES can add a few points (degrees of freedom) of data to each simplex to form a complex. However, too few points can cause "data clumping" and too many points can compensate the efficacy of GSMILES. Data clumping occurs when the decay constant is too high for a particular data location of a data point or cluster of data points, so that it tends to be isolated from the rest of the data and cannot link properly due to insufficient overlap with other nodes. This results in a spike node at that location that cannot interpolate or predict properly within its adjacent domain region. In summary, data clumping can be localized as with singular data points, or it can be more global in terms of distribution of data clusters.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, system, process, process step or steps, algorithm, hardware or software, to the objective, spirit and scope of the present invention. All such modifications are intended to be within the scope of the claims appended hereto.

That which is claimed is:

1. A method of generating a predictor model for predicting multivariable outcomes based upon multivariable inputs with consideration of nuisance variables, said method comprising the steps of:
   a) defining an initial model as Model Zero and inputting Model Zero as column one of a similarity matrix T;
   b) performing an optimization procedure to solve for matrix values of an $\alpha$ matrix which is a transformation of outcome profiles associated with input profiles, wherein the outcome profiles are calculatable for continuous variables, logistic variables, and ordinal variables;
   c) calculating a residual matrix $\epsilon$ based on the difference between the actual outcome values and the predicted outcome values determined through a product of matrix T and matrix $\alpha$;
   d) selecting a row of the residual matrix $\epsilon$ which contains an error value most closely matching a pre-defined error criterion;
   e) identifying a row from a matrix of the multivariable inputs which corresponds to the selected row from the residual matrix $\epsilon$;
   f) calculating similarity values between the identified row and each of the rows in the matrix of the multivariable inputs, including the identified row with itself;
   g) populating the next column of similarity matrix T with the calculated similarity values if it is determined that the identified row is not collinear or nearly collinear with any previously identified row the similarity values for which were used to populate a previous column of similarity matrix T;
   h) repeating steps b) through g) until a predefined stopping criterion has been reached; and
   i) performing at least one of storing and outputting the predictor model defined by the similarity matrix T resulting from carrying out steps (a)–(h).

2. The method of claim 1, wherein the step of performing an optimization procedure comprises performing a least squares regression procedure.

3. A method comprising forwarding a result obtained from the method of claim 1, to a remote location.

4. A method comprising transmitting data representing a result obtained from the method of claim 1 to a remote location.

5. A method comprising receiving a result obtained from a method of claim 1 from a remote location.

6. The method of claim 1, wherein the predefined stopping criterion comprises a determination that all error criteria of the residual matrix are within bounds of a predefined error threshold having been predefined as acceptable for an intended application of the model.

7. The method of claim 1, wherein the predefined stopping criterion comprises determining that all remaining rows of the matrix of multivariable inputs which have not been used to calculate similarity values to populate a column of matrix T are collinear or nearly collinear with at least one of the rows of the matrix of multivariable inputs which have been used to calculate similarity values to populate a column of matrix T.

8. The method of claim 1, further comprising trimming the number of columns in the T matrix to an optimized minimum number to optimize prospective predictions.

9. The method of claim 1, wherein the pre-defined error criterion comprises maximum absolute ensemble error.

10. The method of claim 1, wherein the pre-defined error criterion is selected from the group consisting of: mean absolute ensemble error, median absolute ensemble error, mode absolute ensemble error, weighted average absolute ensemble error, and robust average absolute ensemble error.

11. The method of claim 1, further comprising estimating validation error of the model derived using the leave-one-out (LOO) cross validation technique.

12. The method of claim 11, wherein the leave-one-out (LOO) cross validation technique enables viable computation of the variance in the validation error according to the formula:

$$\sigma_{LOO}^2 = \frac{1}{n}\sum_{i=1}^{n}\left(\frac{\rho_i}{P_{ii}}\right)^2$$

where
$\sigma_{LOO}^2$ is the predicted variance in the validation error,
n is the number of profiles of multivariable inputs and multivariable outputs,
$\rho_i$ is a residual value corresponding to the $i^{th}$ profile of multivariable inputs and outputs, and
$P_{ii}$ is the diagonal of the projection matrix corresponding to the $i^{th}$ profile.

13. A method of predicting multivariable outcomes (row vectors, called Y-profiles) in an outcome-variable matrix Y using matched profiles of multivariable inputs (row vectors, called X-profiles) in an input-data matrix X, said method comprising:
  adding n row vectors of X-profiles and Y-profiles, respectively, to the input and outcome profiles used to determine the predictor model of claim 1,
  adding n rows of values to Model Zero;
  calculating similarity values for each of the n rows of X-profiles with each of the identified rows used to calculate similarity values used in populating columns of matrix T, and adding the calculated similarity values in corresponding positions in an additional n rows in similarity matrix T; and
  multiplying the n rows of the similarity matrix T by the α matrix to arrive at predictions of the Y-profiles, within an acceptable predefined range of; and
  performing at least one of outputting said Y-profiles to a client and storing said Y-profiles, wherein said Y-profiles are calculatable for continuous variables, logistic variables, and ordinal variables.

14. A method of self-predicting multi-variable profiles, comprising the steps of:
  generating the predictor model according to claim 1 through use of X-variable profiles as both the multi-variable inputs and the multivariable outcomes;
  wherein the identified rows populating the similarity matrix T are essential profiles of the prediction model, and wherein the predicted multivariable outcomes smooth the X-variable profiles input function, reduce noise due to the nuisance variables, and restrict candidate profiles in the X-variable profiles to enhance causal leverage between profiles.

15. A method of imputation of missing values in multi-variable X-profile inputs, comprising the steps of:
  a) modifying the multi-variable X-profile inputs by replacing the missing values with initial starting values;
  b) self-predicting multi-variable X-profile outputs of the modified multi-variable inputs according to the method of claim 14;
  c) replacing the modifications to the missing variables with the predicted variables obtained by self-predicting multi-variable X-profile outputs in step b); and
  repeating steps b) and c) until differences between the current replacement modifications and the previous iteration of replacement modifications are less than a pre-defined threshold value of correction difference.

16. A method of simultaneously predicting both multi-variable X-input profiles and multi variable Y-output profiles based on the multi-variable X-input profiles, said method comprising the steps of:
  generating the predictor model according to claim 1 through use of the X-variable profiles as the multivariable inputs and both the X-variable profiles and Y-variable profiles as the multivariable outputs.

17. The method of claim 16, wherein the X-variable profiles and Y-variable profiles are stacked vertically to form a combined matrix of the multivariable outputs.

18. The method of claim 16, wherein the X-variable profiles and Y-variable profiles are concatenated horizontally to form a combined matrix of the multivariable outputs.

19. The method of claim 16, wherein the identified rows used to calculate similarity values used in populating columns of matrix T are strategic X-profile rows, and wherein said method further comprises clustering the strategic X-profile rows in a combined matrix defining both the X-variable profiles and Y-variable profiles.

20. A method of simultaneously predicting both multi-variable X-input profiles and multi variable Y-output profiles based on the multi-variable X-input profiles and the multi-variable Y-output files, said method comprising the of:
  generating the predictor model according to claim 1 through use of an X/Y matrix, resulting from the catenation of the X-variable profiles and Y-variable profiles, as the multivariable inputs and using the X/Y matrix as the multivariable outputs.

21. The method of claim 20, wherein said step of identifying a row is restricted to only the X-profile portion of the X/Y input matrix, resulting in enhanced causal leverage between the X- and Y-profiles.

22. The method of claim 1, further comprising assigning score functions to the multi-variable outcomes for use in any multivariate distribution process; and
  performing at least one of storing and outputting the score functions to a client.

23. The method of claim 1, further comprising testing the ellipticity of the identified rows of X-profiles as a function of the X-space, using the Marquardt-Levenberg algorithm, and ranking the X-variable in the identified rows of X-profiles according to said testing.

24. The method of claim 1, further comprising determining a decay constant for each of the identified rows of X-profiles used to calculate similarity values to populate the T matrix.

25. The method of claim 24, wherein the step of determining a decay constant for each of the identified rows comprises the steps of:
   determining the working dimension of the domain for each data location of the multi-variable data;
   computing a domain simplex of data adjacent to each said data location; and
   setting each decay constant as the inverse of a largest of dissimilarity values calculated between each data location and the domain simplex of the data adjacent to that data location.

26. The method of claim 25, further comprising adding data points to each domain simplex to form a domain complex.

27. A computer-readable medium carrying one or more sequences of instructions from a user of a computer system for predicting multivariable outcomes based upon multivariable inputs with consideration of nuisance variables, wherein the execution of the one or more sequences of instructions by one or more processors cause the one or more processors to perform the steps of:
   a) defining an initial model as Model Zero and inputting Model Zero as column one of a similarity matrix T;
   b) performing an optimization procedure to solve for matrix values of an α matrix which is a transformation of outcome profiles associated with input profiles;
   c) calculating a residual matrix ϵ based on the difference between the actual outcome values and the predicted outcome values determined through product of matrix T and matrix α;
   d) selecting a row of the a residual matrix ϵ which contains an error value most closely matching a predefined error criterion;
   e) identifying a row from a matrix of the multivariable inputs which corresponds to the selected row from the residual matrix ϵ;
   f) calculating similarity values between the identified row and each of the rows in the matrix of the multivariable inputs, including the identified row with itself;
   g) populating the next column of similarity matrix T with the calculated similarity values if it is determined that the identified row is not collinear or nearly collinear with any previously identified row the similarity values for which were used to populate a previous column of similarity matrix T; and
   h) repeating steps b) through g) until a predefined stopping criterion has been reached; and
   i) performing at least one of storing and outputting to a client a predictor model defined by the similarity matrix T, wherein the predictor model is calculatable for output variables comprising continuous variables, logistic variables, and ordinal variables.

28. The computer readable medium of claim 27, wherein the following further step is performed: trimming the number of columns in the T matrix to an optimized minimum number to optimize prospective predictions.

29. The computer readable medium of claim 27, wherein the following further step is performed: estimating validation error of the model derived using the leave-one-out (LOO) cross validation technique, according to the formula:

$$\sigma_{LOO}^2 = \frac{1}{n}\sum_{i=1}^{n}\left(\frac{\rho_i}{P_{ii}}\right)^2$$

where
   $\sigma_{LOO}^2$ is the predicted variance in the validation error,
   n is the number of profiles of multivariable inputs and multivariable outputs,
   $\rho_i$ is a residual value corresponding to the $i^{th}$ profile of multivariable inputs and outputs, and
   $P_{ii}$ is the diagonal of the projection matrix corresponding to the $i^{th}$ profile.

* * * * *